US012611448B2

(12) United States Patent
Liu

(10) Patent No.: US 12,611,448 B2

(45) Date of Patent: Apr. 28, 2026

---

(54) TARGETING DELIVERY SYSTEM LOADED WITH WHOLE-CELL COMPONENTS AND USE THEREOF

(71) Applicant: SUZHOU ERSHENG BIOPHARMACEUTICAL CO., LTD, Suzhou (CN)

(72) Inventor: Mi Liu, Suzhou (CN)

(73) Assignee: SUZHOU ERSHENG BIOPHARMACEUTICAL CO., LTD, Suzhou (CN)

( * ) Notice: Subject to any disclaimer, the term of this patent is extended or adjusted under 35 U.S.C. 154(b) by 523 days.

(21) Appl. No.: 18/028,084

(22) PCT Filed: Nov. 5, 2020

(86) PCT No.: PCT/CN2020/126655

§ 371 (c)(1),
(2) Date: Mar. 23, 2023

(87) PCT Pub. No.: WO2022/082869

PCT Pub. Date: Apr. 28, 2022

(65) Prior Publication Data

US 2023/0330199 A1 Oct. 19, 2023

(30) Foreign Application Priority Data

Oct. 23, 2020 (CN) .......................... 202011146241.9

(51) Int. Cl.
| | |
|---|---|
| *A61K 39/00* | (2006.01) |
| *A61K 9/51* | (2006.01) |
| *A61K 39/39* | (2006.01) |
| *A61P 37/04* | (2006.01) |

(52) U.S. Cl.
CPC .... *A61K 39/001102* (2018.08); *A61K 9/5153* (2013.01); *A61K 39/39* (2013.01); *A61P 37/04* (2018.01); *A61K 2039/5154* (2013.01); *A61K 2039/55555* (2013.01); *A61K 2039/55561* (2013.01)

(58) Field of Classification Search
None
See application file for complete search history.

(56) References Cited

U.S. PATENT DOCUMENTS

2023/0121878 A1 4/2023 Liu

FOREIGN PATENT DOCUMENTS

| | | | |
|---|---|---|---|
| AU | 2010242374 A1 | 11/2011 | |
| CN | 108992666 A | 12/2018 | |
| CN | 109865134 A | 6/2019 | |
| EP | 3903787 A1 * | 11/2021 | ......... A61K 39/0011 |

| | | |
|---|---|---|
| JP | 2023534577 A | 8/2023 |
| WO | WO-2010126081 A1 | 11/2010 |
| WO | WO-2012054807 A2 | 4/2012 |
| WO | WO-2016081783 A1 | 5/2016 |

OTHER PUBLICATIONS

Jun. 25, 2024 First Office Action issued in Japanese Patent Application No. 2023-521074.

Tae In Wi et al., "Selective Tumor-Specific Antigen Delivery to Dendritic Cells Using Mannose-Labeled Poly(d,l-lactide-coglycolide) Nanoparticles for Cancer Immunotherapy", J of Biomedical Nanotechnology, vol. 16, 201-211, 2020, pp. 201-211.

Jul. 21, 2021 International Search Report issued in International Patent Application No. PCT/CN2020/126655.

Jul. 21, 2021 Written Opinion of the International Searching Authority issued in International Patent Application No. PCT/CN2020/126655.

Yang, Xiaomei et al. "Anti-Tumor Activity of Mannose-CpG-Oligodeoxynucleoti-des-Conjugated and Hepatoma Lysate-Loaded Nanoliposomes for Targeting Dend Ritic Cells In Vivo." Journal of Biomedical Nanotechnology., vol. 15(5), p. 1018-1032(Dec. 31, 2019).

Shi, Gaona et al. "Enhanced antitumor immunity by targeting dendritic cells with tumor cell lysate-loaded chitosan nanoparticles vaccine." Biomaterials., vol. 113, p. 191-202 (Oct. 29, 2016).

(Continued)

*Primary Examiner* — Daniel C Gamett

(74) *Attorney, Agent, or Firm* — Harness, Dickey & Pierce, P.L.C.

(57) ABSTRACT

A targeting delivery system loaded with whole-cell components, which relates to the technical field of immunotherapy. The targeting delivery system is a nano-sized or micron-sized particle with a target head on the surface, and the particle is loaded with whole-cell components of cancer cells or cancer tissues; the whole-cell components are water-soluble ingredients and water-insoluble ingredients of whole cells in cells or tissues, and the water-insoluble ingredients are dissolved by a solubilizer; and the target head binds to a molecule on the surface of a specific cell or tissue, so as to help the particle to enter the cell or tissue. According to the targeting delivery system, a specific solubilizer is used to solubilize the water-insoluble part, which allows same to be dissolved in an aqueous solution, so that the whole-cell antigens of the water-soluble ingredients and the water-insoluble ingredients in cancer cells or tissues can be combined to prepare a cancer vaccine. In addition, the target head capable of targeting antigen-presenting cells is added to improve the phagocytosis efficiency of the antigen-presenting cells in an active targeting manner, thereby improving the effect of preventing or treating cancer.

19 Claims, 11 Drawing Sheets

(56) References Cited

OTHER PUBLICATIONS

Runling Wen et al. "Studies on Solubilization Effects of TritonX-100, DOC and KCI on Tumor Cell Membrane Antigens" Journal of Ningxia Medical University., vol. 10(4), p. 14-18 (Dec. 31, 1988).

* cited by examiner

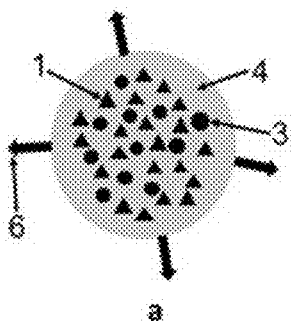

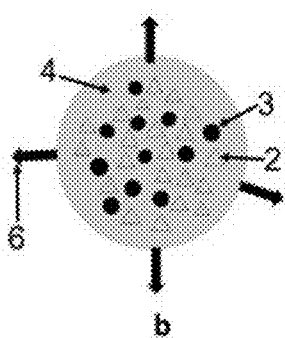

a b

PBS blank control

Nano-vaccine 1 (water-soluble components) +nano-vaccine 2 (PEG solubilized components)

Nano-vaccine 1 (water-soluble components) + nano-vaccine 2 (6 M guanidine hydrochloride solubilized components)

PBS control group

Nano-vaccine 1 (water-soluble components) +nano-vaccine 2 (PEG solubilized components)

Nano-vaccine 1 (water-soluble components) + nano-vaccine 2 (6 M guanidine hydrochloride solubilized components)

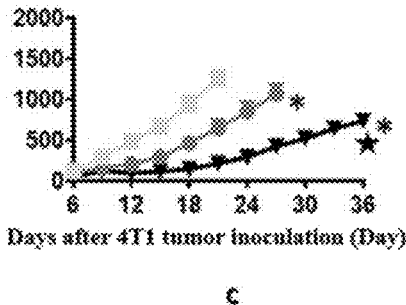

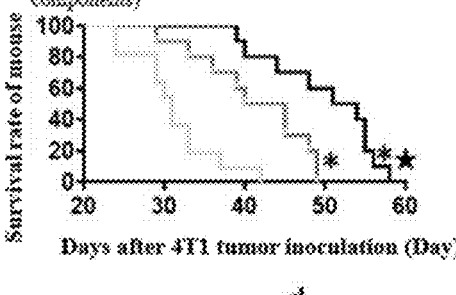

TARGETING DELIVERY SYSTEM LOADED WITH WHOLE-CELL COMPONENTS AND USE THEREOF

CROSS-REFERENCE TO RELATED APPLICATIONS

This application is a U.S. National Phase Application under 35 U.S.C. 371 of International Application No. PCT/CN2020/126655, filed on Nov. 5, 2020, which claims the priority of the Chinese patent application filed to China National Intellectual Property Administration on Oct. 23, 2020, with an application number of 202011146241.9, entitled "TARGETING DELIVERY SYSTEM LOADED WITH WHOLE-CELL COMPONENTS AND USE THEREOF", the entire contents of which is incorporated herein by reference.

TECHNICAL FIELD

The present disclosure relates to the field of immunotherapy, specifically relates to a targeting delivery system loaded with whole-cell components and use thereof.

BACKGROUND

Immunity is a physiological function of the human body that allows the body to recognize "self" and "non-self" components and thus destroy and repel antigen substances (such as viruses and bacteria) that enter the body, or damaged cells and tumor cells produced by the body itself, in order to maintain the body health. Immunological technology has been developed extremely rapidly in recent years, particularly in the field of cancer immunotherapy. With the increasing understanding of cancer, it has been discovered that the body's immune system and various types of immune cells play pivotal roles in inhibiting the development and progression of cancer.

Cancer immunotherapy has been developed rapidly in recent years, and cancer vaccine is one of the important approaches for cancer immunotherapy and prevention. Effective cancer vaccine requires the loading of cancer-specific antigens and efficient delivery of these loaded antigens to antigen-presenting cells for activating the body's immune system to recognize and attack cancer cells. Currently, scientists have analyzed and identified cancer-specific or cancer-associated antigenic peptides from tumor cells of cancer patients, and then synthesized them in vitro to prepare cancer vaccines for cancer treatment. This approach has shown a certain curative effect in clinical trials of cancer patients. However, the number of cancer antigens that can be found by this type of method is limited, and it is time-consuming and costly, while the resulting peptides vaccines have no ability to target antigen-presenting cells (APCs).

In order to give full play to the function of vaccines, antigens need to be delivered and presented to antigen-presenting cells, which then process the cancer antigens and present them to the surface of the antigen-presenting cells, and interact with T cells to activate the immune recognition ability of T cells to cancer cells. Once T cells can recognize specific cancer antigens, they will recognize and kill the cancer cells that contain these cancer antigens.

Moreover, current technology uses only a limited number of antigens, which cannot cover the vast majority of cancer antigens in patients. Because of the diversity of both cancer cells antigens and cancer mutations, the cancer cells antigens in each patient are different even in the same kind of cancer. As a result, it is difficult to prepare cancer vaccines for most people through a limited number of cancer cells antigens. Cancer cells and tumor tissues from patients contain cancer antigens and mutations that are unique to each individual, and thus are personalized antigens, and the prepared cancer vaccines therefrom are also personalized vaccines. Tumor tissues contain various types of cancer antigens, and if tumor tissues or whole-cell components of cancer cells can be delivered to antigen-presenting cells as vaccines, then vaccines will have favorable preventive and therapeutic effects on cancer. However, due to the limitation of current technology, researchers have to focus on water-soluble components, but cannot effectively apply water-insoluble components, which is the difficulty in the application of whole-cell components at present.

In addition, in order to give full play to the function of vaccines, antigens need to be delivered and presented to antigen-presenting cells first, and after being processed by antigen presenting cells, the cancer antigens are presented to the surface of the antigen-presenting cells and interact with T cells to activate the immune recognition of cancer cells of T cells. Once T cells recognize the specific cancer antigens, they will further recognize and kill the cancer cells containing these cancer antigens. Currently, targeting antigen-presenting cells by particle size is called passive targeting. However, the cancer antigens cannot be high efficiently present to the surface of antigen-presenting cells and interact with T cells by passive targeting alone. Taking 300 nm nanoparticles as an example, it can be phagocytosed by antigen-presenting cells such as dendritic cells and B cells, meanwhile can also be phagocytosed by other cells such as fibroblasts.

Content of the Present Invention

In view of this, the purpose of the present invention is to provide a targeting delivery system loaded with whole-cell components, so that the targeting delivery system can present whole-cell components, comprising the water-soluble and water-insoluble components of cancer cells or tissues, to antigen-presenting cells in an active targeting way, which can improve the efficacy of preventing and treating tumors.

Another purpose of the present invention is to provide a use of the targeting delivery system described above in the preparation of vaccines for preventing and/or treating of cancer.

In order to achieve the purpose, the present invention provides the following technical solutions:

A targeting delivery system loaded with whole-cell components, which is a nano-sized or micron-sized particles with a targeting head on surface thereof, and the particles are loaded with whole-cell components of cancer cells or cancer tissues, while water-insoluble components are solubilized with the solubilizer; the whole-cell components are water-soluble components and water-insoluble components of whole cells in the cells or tissues; the targeting head bonds to molecules on surface of specific cells or tissues to assist the particles to enter cells or tissues.

In the present invention, after lysing cancer cells or tissues, water-soluble components that are soluble in pure water or an aqueous solution without a solubilizer are first obtained, and then water-insoluble components are solubilized in a solubilizing solution with a solubilizing aqueous solution containing a solubilizer. In this way, all cellular components can be converted to components that are soluble in an aqueous solution, and then loaded inside and outside of nanoparticles or micron-particles to prepare targeting delivery system, thereby ensuring that the vast majority of antigen substances are loaded onto the prepared the targeting delivery system. In practice, whole-cell components can be directly solubilized with a solubilizing aqueous solution containing a solubilizer after lysing cells or tissues without collecting the water-soluble and water-insoluble components separately, and the whole cell components solubilized with the solubilizing aqueous solution can be used to prepare a targeting delivery system.

Water-soluble and water-insoluble components of cell components in cancer cells or tumor tissues encompasses constituents and components of whole-cell. Wherein the unmutated proteins, peptides and genes that are the same as the normal cell components will not cause an immune response because of the immune tolerance induced during the development of the body immune system; mutations of genes, proteins and peptides generated by cancer are immunogenic and can activate the body's immune response against cancer cells due to the lack of immune tolerance induced during the development of the body immune system. These substances in the whole-cell components, gifted with cancer cell-specific immunogenicity induced by disease mutations, can be used for cancer prevention and treatment.

In the targeting delivery system of the present invention, the whole-cell components can be divided into two portions according to the solubility in pure water or an aqueous solution without a solubilizer: a water-soluble component and a water-insoluble component. The water-soluble component is the original water-soluble portion that is soluble in pure water or an aqueous solution without a solubilizer, and the water-insoluble component is the original water-insoluble portion that is insoluble in pure water. The portion of the water-insoluble component that is insoluble in pure water or an aqueous solution without a solubilizer can be converted to being soluble in an aqueous solution containing a solubilizer by an appropriate solubilization method. Both water-soluble components and water-insoluble components in the whole-cell components can be solubilized with a solubilizing aqueous solution containing a solubilizer.

In the targeting delivery system of the present invention, wherein the solubilizer include but not limited to urea, guanidine hydrochloride, sodium deoxycholate, SDS, glycerol, alkaline solution with a pH larger than 7, acidic solution with a pH less than 7, various protein degrading enzymes, albumin, lecithin, inorganic salts at high concentrations, Triton, Tween, DMSO, acetonitrile, ethanol, methanol, DMF, propanol, isopropanol, acetic acid, cholesterol, amino acids, glycosides, choline, Brij™-35, Octaethylene glycol monododecyl ether, CHAPS, Digitonin, lauryldimethylamine oxide, IGEPAL® CA-630, DMSO, acetonitrile, ethanol, methanol, DMF, isopropanol, propanol, dichloromethane and ethyl acetate. One or more of them can be selected.

The water-insoluble component can also be converted from insoluble to soluble in pure water by other methods that can solubilize protein and peptide fragments. But in the specific embodiment of the present invention, the effects of urea, guanidine hydrochloride, SDS, sodium deoxycholate or glycerol are obviously better than other solubilizers such as PEG. Preferably, the present invention uses a solubilizing solution containing urea or guanidine hydrochloride to directly lyse cells or tissues to directly solubilize whole-cell components. In the listed examples of the present invention, 8 M urea and 6 M guanidine hydrochloride aqueous solution are used to solubilize the water-insoluble components in tumor tissues or cancer cells. In practice, any other solubilizing solutions such as SDS and glycerol that can solubilize water-insoluble components of whole-cell components can also be used.

Micron-particles or nanoparticles have an optimal particles size for targeting antigen-presenting cells, but the optimal size of nanoparticles or micron-particles prepared by different materials may vary. For example, the optimal size of cationic liposomes is currently considered to be around 50-150 nm, and that of nanoparticles prepared by PLGA may be around 200-500 nm. However, micron-particles are theoretically considered to be optimal with size around 1.5-5 Such optimal size varies depending on the particles materials. Targeting antigen-presenting cells by particles size is called passive targeting.

In addition to apply passive targeting, the present invention also provides an active targeting strategy, i.e., a targeting head molecule that can target specific cells is connected outside the nanoparticles or micron-particles. In this way, nanoparticles or micron-particles can be directly targeted to the surface of specific cells or tissues, and the particles are assisted to enter cells or tissues through ligand-receptor binding. These cells include, but are not limited to dendritic cells, macrophages, B cells, T cells, NK cells, NKT cells, neutrophils, eosinophils and basophils in leukocytes. Tissues to which the targeting head can target include, but are not limited to, lymph nodes, thymus, spleen and bone marrow. These cell and tissues can be targeted by molecules including but not limit to mannose, mannan, CD32 antibody, CD11c antibody, BDCA-1 antibody, CD141 antibody, CD123 antibody, CD14 antibody, CD19 antibody, CD20 antibody, CD103 antibody, CD11b antibody, CD33 antibody, CD40 antibody, CD40L antibody, CD80 antibody, CD86 antibody.

For example, relying solely on passive targeting, nanoparticles, having a particle size of 300 nm, can be phagocytosed by antigen-presenting cells such as dendritic cells, B cells and the like, but may also be phagocytosed by other cells such as fibroblasts and the like. In contrast, if an active targeting strategy is used, it is targetedly phagocytosed by the most critical antigen-presenting cells such as dendritic cells. In the listed example of the present invention, mannose (i.e., targeting head)-modified nanoparticles or micron-particles target dendritic cells. In practice, any targeting head that can target dendritic cells or other types of specific cells or tissues can also be used.

The particle size of nano-vaccine or micron-vaccine is nano-scale or micron-scale, thereby ensuring that the vaccine is phagocytosed by antigen-presenting cells, and in order to improve the phagocytosis efficiency, the particle size should be within an appropriate range. In the targeting delivery system of the present invention, nano-sized particles have a particle size of 1 nm-1000 nm. In some embodiments, the nano-sized particles have a particle size of 30 nm-800 nm. Further, in some embodiments, the nano-sized particles have a particle size of 50 nm-600 nm.

In the targeting delivery system of the present invention, micron-sized particles have a particle size of 1 μm-1000 μm. In some embodiments, the micron-sized particles have a particle size of 1 μm to 100 μm. In some embodiments, the micron-sized particles have a particle size of 1 μm to 10 μm. Further, in some embodiments, the micron-sized particles have a particle size of 1 μm-5 μm.

In the delivery system of the present invention, the surface of the nano-sized particles or micron-sized particles can be electrically neutral, negatively charged or positively charged.

In order to enhance the immunogenicity and efficacy of the targeting delivery system, some immune adjuvants, having the function of immunomodulation, can also be added, such as pattern recognition receptor agonist, Bacille Calmette-Guerin (BCG) cell wall skeleton, residues from methanol extraction of BCG, BCG muramyl dipeptide, *Mycobacterium phlei*, polyresistin, mineral oil, virus-like particles, immune enhanced reconstituted influenza virus bodies, cholera enterotoxin, saponin and derivatives thereof, Resiquimod, thymosin, newborn bovine liver active peptides, imiquimod, polysaccharides, curcumin, immune adjuvant poly ICLC, *Corynebacterium parvum* vaccine, *Streptococcus hemolyticus* preparations, coenzyme Q10, levamisole, Polycytidylic acid, interleukin, interferon, Polyinosinic acid, Polyadenosinic acid, alum, aluminium phosphate, lanolin, vegetable oil, endotoxin, liposome adjuvants, GM-CSF, MF59, double-stranded RNA, double-stranded DNA, aluminum hydroxide, CAF01, active ingredients of traditional Chinese medicine such as *ginseng* and *Astragalus membranaceus*. One or more of them can be selected. Methods for adding the immune adjuvants of the present invention include loading it inside nanoparticles or micron-particles, or loading it onto the surface of nanoparticles or micron-particles, or loading it both inside and onto the surface of nanoparticles or micron-particles. Preferably, the immune adjuvants are added into whole-cell components.

In a specific embodiment of the present invention, Polyinosinic-polycytidylic acid (poly(I:C)), *Bacillus* Calmette-Guerin (BCG) or CpG is added as immune adjuvants into water-soluble components and solubilized water-insoluble components (that is original water-insoluble and solubilized with solubilizing solution with a solubilizer) of cancer cells lysate or tumor tissues lysate. Preferably, the concentration of poly(I:C), BCG or CpG is larger than 1 ng/mL.

In order to improve the targeting ability and efficacy of the targeting delivery system, the present invention also comprising adding a PEG protective film outside the particles.

In the targeting delivery system of the present invention, materials for preparing the nano-sized or micron-sized particles are one or more of organic synthetic polymer materials, natural polymer materials, inorganic materials, bacteria or viruses.

Wherein, the organic synthetic polymer materials are biocompatible or degradable polymer materials, including but not limited to PLGA, PLA, PGA, Poloxamer, PEG, PCL, PEI, PVA, PVP, PTMC, polyanhydride, PDON, PPDO, PMMA, polyamino acids and synthetic peptides.

The natural polymer materials are biocompatible or degradable polymer materials, including but not limited to phospholipids, cholesterol, starch, carbohydrates, peptides, sodium alginate, albumin, collagen, gelatin, and cell membrane components.

The inorganic materials are materials without obvious biological toxicity, including but not limited to ferric oxide, ferroferric oxide, calcium carbonate, and calcium phosphate.

The shape of the targeting delivery system of the present invention is any common shape, including but not limited to spherical, ellipsoidal, barrel-shaped, polygonal, rod-shaped, flaky, linear, worm-shaped, square, triangular, butterfly-shaped or dish-shaped.

In the targeting delivery system of the present invention, the loading method is that the water-soluble components and the water-insoluble components of whole-cell are loaded separately or together inside the particles, and/or loaded separately or together onto the particles surface, including, but not limited to, the water-soluble components are loaded both inside and onto the surface of the particles; the water-insoluble components are loaded both inside and onto the surface of the particles; the water-soluble components are loaded inside and the water-insoluble components are loaded onto the surface of the particles; the water-insoluble components are loaded inside the particles and the water-soluble components are loaded onto the surface of particles; the water-soluble components and the water-insoluble components are loaded inside the particles, while only the water-insoluble components are loaded onto the surface of particles; the water-soluble components and the water-insoluble component are loaded inside the particles, while only the water-soluble components are loaded onto the surface of particles; the water-soluble components are loaded inside the particles, while the water-soluble components and the water-insoluble components are loaded together onto the surface of particles; the water-insoluble components are loaded inside and the water-soluble components and the water-insoluble components are loaded together onto the surface of particles; the water-soluble components and the water-insoluble components are loaded together inside the particles and the water-soluble components and the water-insoluble components are loaded together onto the surface of particles.

A schematic diagram of the structure of the delivery system loaded with whole-cell components of the present invention are shown in FIGS. 2-17. In practice, one of nanoparticles or micron-particles with a specific structure may be used alone, or two or more nanoparticles or micron-particles with different structures may be used simultaneously.

The targeting delivery system of the present invention can be prepared by any known preparation method of nano-sized particles and micron-sized particles. The methods include but not limited to common solvent evaporation method, dialysis method, extrusion method, and heat melt methods. In some embodiments, the delivery system is prepared by a double-emulsion method of the solvent evaporation method.

The targeting delivery system loaded with whole-cell components of the present invention can deliver the loaded whole-cell components to the relevant immune cells, and activate and enhance the killing efficacy of the body's immune system on cancer cells through the immunogenicity of the loaded components. Therefore, the present invention also provides a use of the targeting delivery system loaded with whole-cell components in the preparation of a vaccine for preventing and/or treating cancer.

Wherein, the cancer is solid tumor or hematological tumor, including but not limited to endocrine system tumor, nervous system tumor, reproductive system tumor, digestive system tumor urinary system tumor, immune system tumor, circulatory system tumor, respiratory system tumor, blood system tumor and skin system tumor.

When used as a cancer vaccine for preventing and treating cancer, the targeting delivery system of the present invention can be administered multiple times before or after the occurrence of cancer to activate the body's immune system, thereby delaying the progression of cancer, treating cancer or preventing cancer recurrence.

It can be seen from the technical solutions described above, the present invention converts the components in cells that are insoluble in pure water or in an aqueous solution without a solubilizer to being soluble in a specific solubilizing solution by using an aqueous solution containing a specific solubilizer, thus the water-insoluble components can be used to prepare nanoparticles and micron-particles, and thereby the comprehensiveness and immunogenicity of antigen substances or components, loaded onto nanoparticles or micron-particles, are improved. At the same time, a targeting head that can target the antigen-presenting cells is added to improve the phagocytosis efficiency of antigen-presenting cells in an active targeting way, therefore the efficacies of preventing or treating cancer are improved.

BRIEF DESCRIPTION OF THE DRAWINGS

In FIG. 2-FIG. 3, both the surface and the interior of the nanoparticles or micron-particles contain immune adjuvants; in FIG. 4-FIG. 5, the immune adjuvants is only distributed inside the nanoparticles or micron-particles; in FIG. 6-FIG. 7, only the outer surface of nanoparticles or micron-particles contain immune adjuvants; in FIG. 8-FIG. 9, there are no immune adjuvants loaded in the interior and on the outer surface of nanoparticles or micron-particles; in FIG. 10, cell components and/or immune adjuvants are only distributed inside the nanoparticles or micron-particles; in FIG. 11, cell components and/or immune adjuvants are only distributed outside the nanoparticles or micron-particles; in FIG. 12, cell components and immune adjuvants are distributed inside or outside the nanoparticles or micron-particles, respectively;

In FIG. 2-9, 2.*a*-2.*i* in FIG. 2, 6.*a*-6.*i* in FIG. 4, 10.*a*-10.*i* in FIGS. 6 and 14.*a*-14.*i* in FIG. 8, when the water-soluble components or water-insoluble components of cells or tissues components, loaded onto the nanoparticles or micron-particles, are distributed inside the nanoparticles or micron-particles, no obvious inner core is formed; 3.*a*-3.*i* in FIG. 2, 7.*a*-7.*i* in FIG. 4, 11.*a*-11.*i* in FIGS. 6 and 15.*a*-15.*i* in FIG. 8, the water-soluble components or water-insoluble components of cells or tissues, loaded onto the nanoparticles or micron-particles, are distributed inside an inner core of the nanoparticles or micron-particles; 4.*a*-4.*i* in FIG. 3, 8.*a*-8.*i* in FIG. 5, 12.*a*-12.*i* in FIGS. 7 and 16.*a*-16.*i* in FIG. 9, the water-soluble components or water-insoluble components of cells or tissues components, loaded onto the nanoparticles or micron-particles, are distributed inside a plurality of inner cores of nanoparticles or micron-particles; 5.*a*-5.*i* in FIG. 3, 9.*a*-9.*i* in FIG. 5, 13.*a*-13.*i* in FIGS. 7 and 17.*a*-17.*i* in FIG. 9, the water-soluble components or water-insoluble components of cells or tissues components, loaded onto the nanoparticles or micron-particles, are distributed on the outer layer of the inner core of nanoparticles or micron-particles; a: the water-soluble components of cells or tissues components are loaded both inside and onto the surface of nanoparticles or micron-particles; b: the water-insoluble components of cells or tissues components are loaded both inside and onto the surface of nanoparticles or micron-particles; c:

the water-insoluble components of cells or tissues components are loaded inside of nanoparticles or micron-particles, while the water-soluble components of cells or tissues components are loaded onto the surface thereof; d: the water-soluble components of cells or tissues components are loaded inside the nanoparticles or micron-particles, while the water-insoluble components of cells or tissues components are loaded onto the surface thereof; e: the water-soluble components and water-insoluble components of cells or tissues components are loaded together inside the nanoparticles or micron-particles, while water-soluble components and water-insoluble components of cells or tissues components are also loaded together onto the surface of nanoparticles or micron-particles; f: the water-soluble components and water-insoluble components of cells or tissues components are loaded together inside the nanoparticles or micron-particles, while the water-soluble components of cells or tissues components alone are loaded onto the surface of the nanoparticles or micron-particles; g: the water-soluble components and water-insoluble components of cells or tissues components are loaded together inside the nanoparticles or micron-particles, while the water-insoluble components of cells or tissues components alone are loaded onto the surface of the nanoparticles or micron-particles; h: the water-insoluble components of cells or tissues components alone are loaded inside the nanoparticles or micron-particles alone, while the water-soluble components and water-insoluble components of cells or tissues components are together loaded onto the surface of the nanoparticles or micron-particles; i: the water-soluble components of cells or tissues components alone are loaded inside the nanoparticles or micron-particles, while the water-soluble components and water-insoluble components of cells or tissues components are loaded together onto the surface of nanoparticles or micron-particles.

Figure 10:
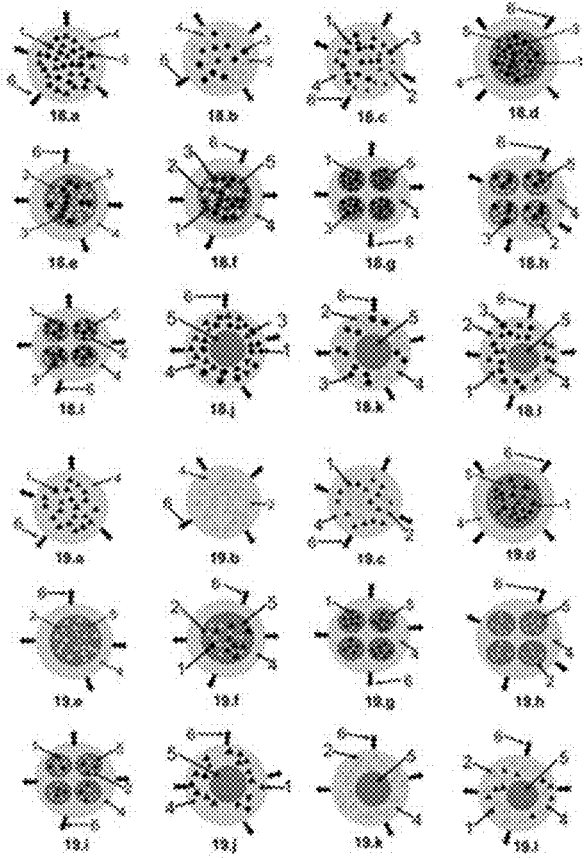
Figure 11:
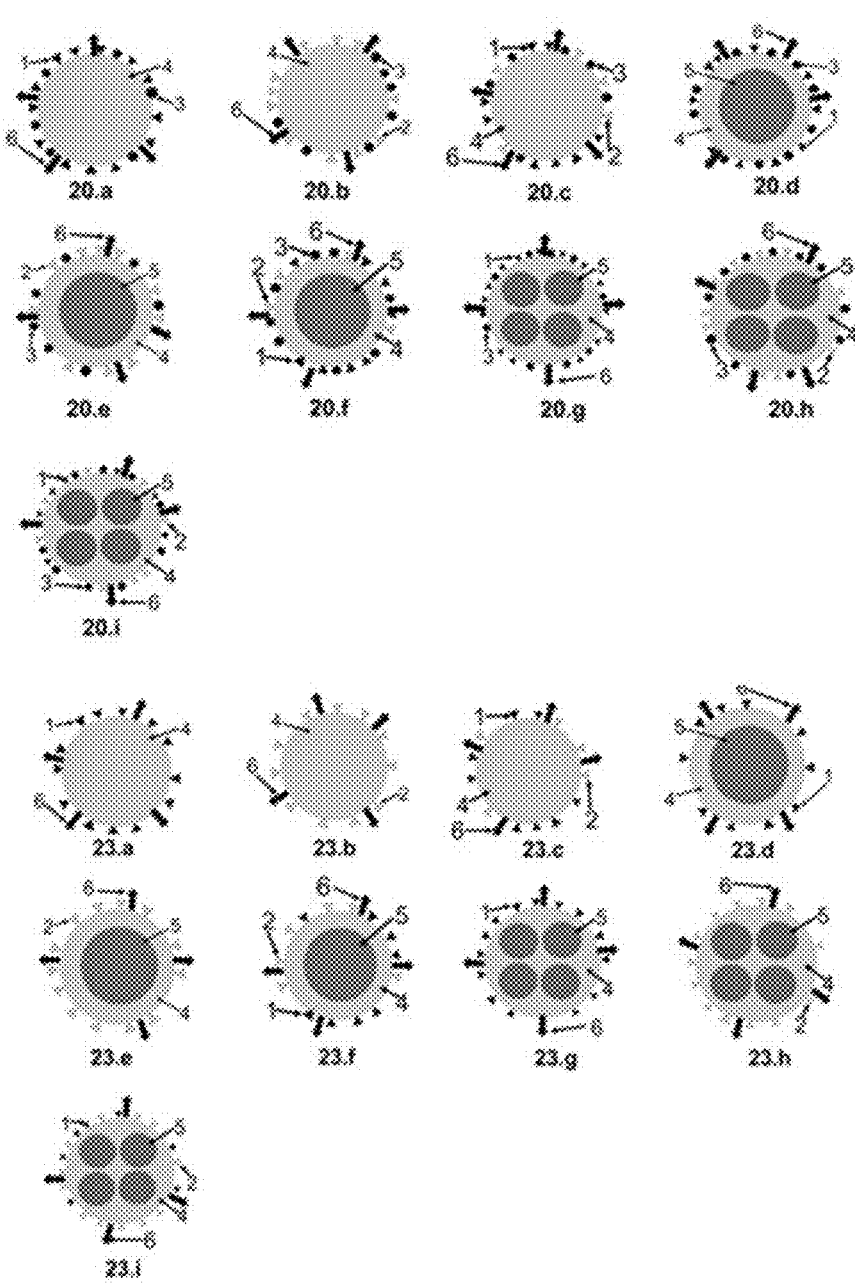
Figure 12:
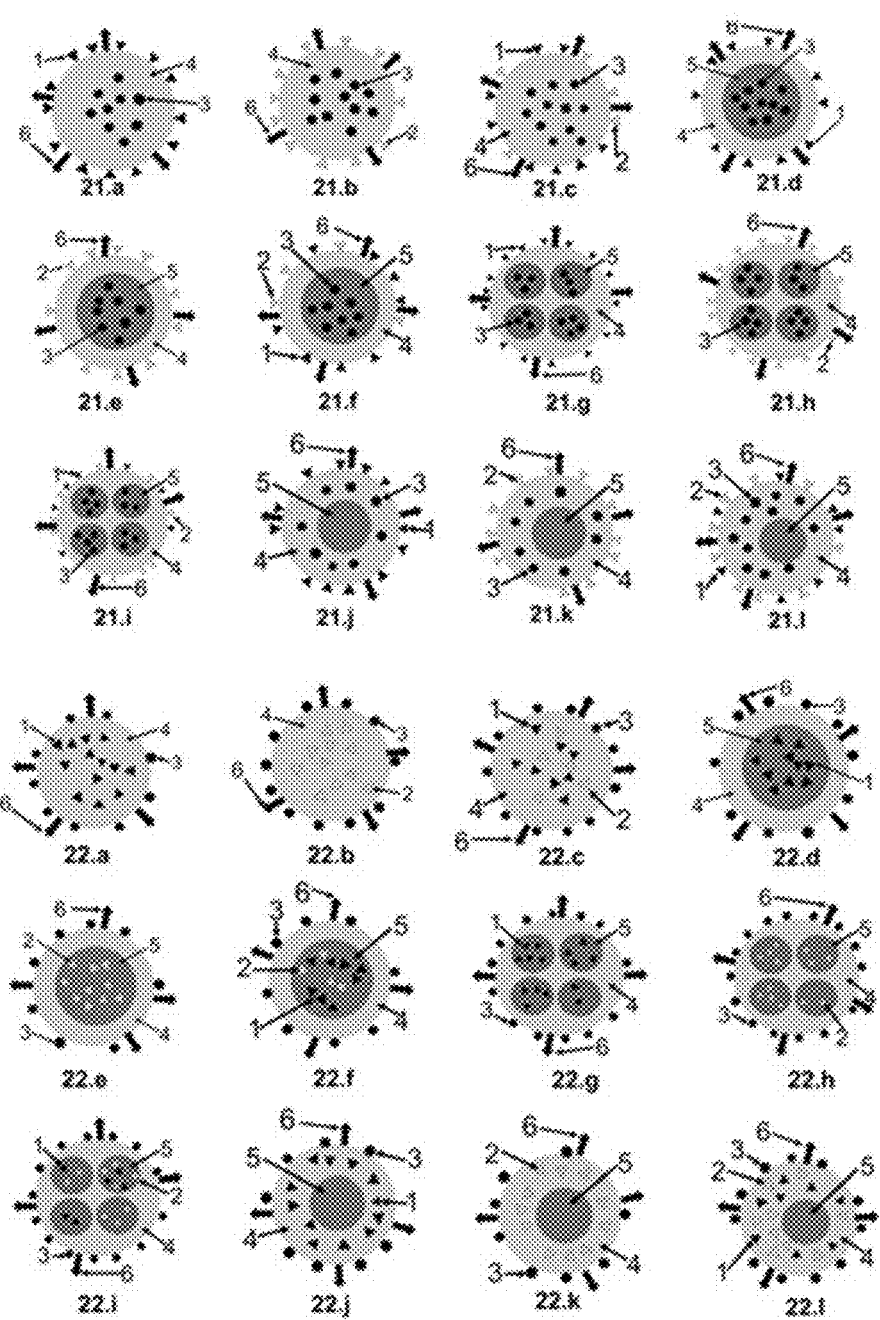

In a, b and c of FIG. 10-12, when the water-soluble or water-insoluble components of cells or tissues components, loaded onto the nanoparticles or micron-particles, are distributed inside the nanoparticles or micron-particles, no obvious inner core is formed; in d, e and f of FIG. 10-12, the water-soluble or water-insoluble components of cells or tissues components loaded onto the nanoparticles or micron-particles are distributed inside one inner core of the nanoparticles or micron-particles; in g, h and i of FIG. 10-12, the water-soluble or water-insoluble components of cells or tissues components loaded onto the nanoparticles or micron-particles are distributed in a plurality of inner cores inside the nanoparticles or micron-particles; in j, k and l of FIG. 10-12, the water-soluble or water-insoluble components of cells or tissues components loaded onto the nanoparticles or micron-particles are distributed in outer layer of the inner cores of nanoparticles or micron-particles; in a, d, g and j of FIG. 10-12, the water-soluble components of cell or tissues components are loaded onto the nanoparticles or micron-particles; in b, e, h and k of FIG. 10-12, water-insoluble components of cells or tissues components are loaded onto the nanoparticles or micron-particles; in c, f, i and l of FIG. 10-12, the water-soluble and water-insoluble components of cells or tissues components are loaded together onto the nanoparticles or micron-particles;

FIGS. 13-19 show the results of targeting nanoparticles or micron-particles for use in cancer treatment and prevention in Examples 1-7, wherein the targeting nanoparticles or micron-particles loaded with whole-cell components of tumor tissues or cancer cells; a, structure of the targeting nanoparticles or micron-particles loaded with water-soluble components/or together water-insoluble components of whole-cell components of tumor tissues or cancer cells; b, structure of the targeting nanoparticles or micron-particles loaded with water-insoluble components of whole-cell components of tumor tissues or cancer cells components; c, experimental results of tumor growth inhibition of targeting nano-vaccine or micron-vaccine; d, experimental results of survival time of mice. In the experiment results, each data pointed in the Figure of tumor growth inhibition assay is shown with mean±standard error (mean±SEM); n=10 in the tumor growth inhibition assay and the mice survival assay. Significant differences in tumor growth inhibition assay in Figure c were analyzed by ANOVA; significant differences in Figure d were analyzed by Kaplan-Meier and log-rank test; * indicates that this group is significantly different from the PBS control group, $P<0.05$; ☆ indicates that this group is significantly different from the control group of blank nanoparticles or blank micron-particles, $P<0.05$; ✚ indicates that this group is significantly different from the nano-vaccine without PEG protective layer, $P<0.05$; ★ indicates that this group is significantly different from the nano-vaccine prepared with water-insoluble components solubilized with PEG of, $P<0.05$.

DETAILED DESCRIPTION OF THE PREFERRED EMBODIMENT

The Examples of the present invention discloses a targeting delivery system loaded with whole-cell components and use thereof. Those skilled in the art can learn from the content of this text and improve the process parameters appropriately to achieve. It should be particularly pointed out that all similar substitutions and modifications are obvious to those skilled in the art, which are considered to be included in the present invention. The targeting delivery system and use thereof of the present invention have been described by preferred embodiments. Relevant persons can obviously make modifications or appropriate alternations and combinations of the targeting delivery system and use thereof described herein without departing from the content, spirit and scope of the present invention, to achieve and apply the technology of the present invention.

Figure 1:
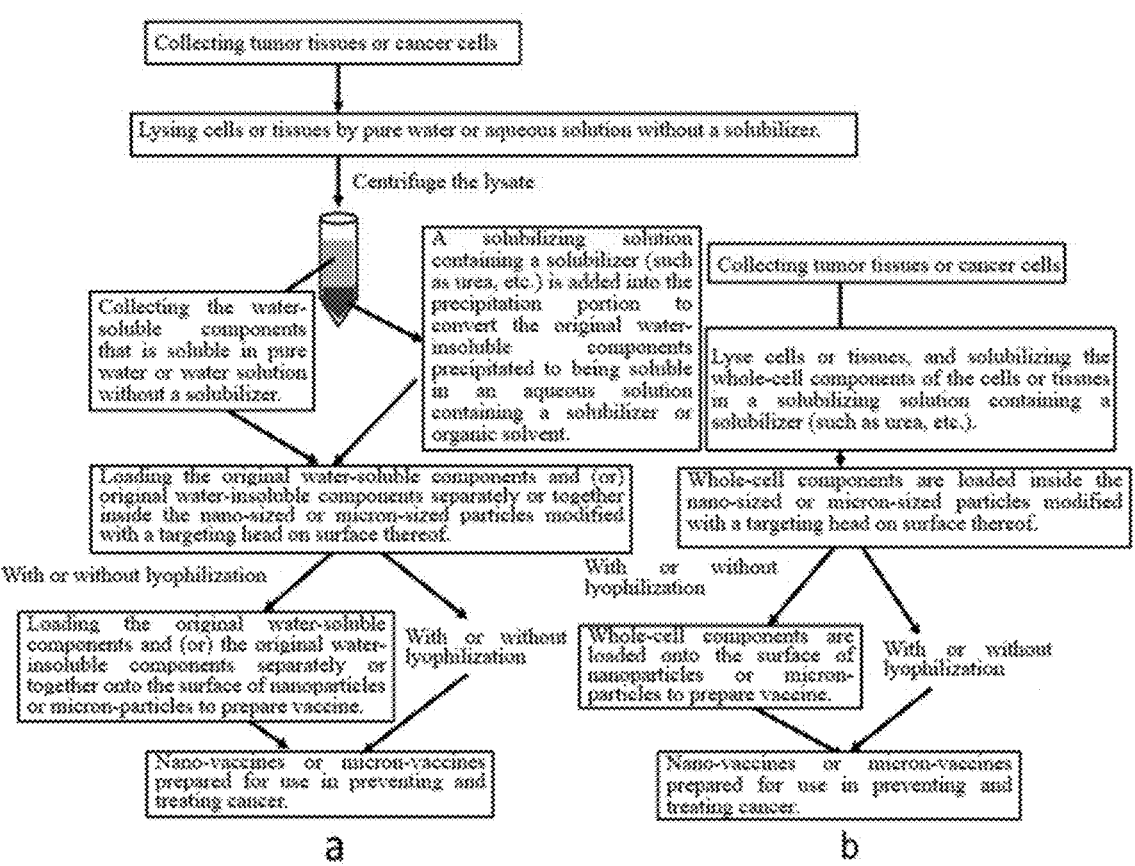
FIG. 1 is the schematic diagram of the preparation process and application fields of the vaccines of the present invention; a: schematic diagram of the collection of water-soluble components and water-insoluble components respectively and preparation of a nano-vaccine or a micron-vaccine; b: schematic diagram of using a solubilizing solution containing a solubilizer to solubilize the whole-cell components and preparing a nano-vaccine or a micron-vaccine.

The targeting delivery system loaded with whole-cell components described in the present invention can be used to prepare vaccines for preventing and/or treating cancer. The preparation process and application fields thereof are shown in FIG. 1. During preparation, water-soluble components and water-insoluble components can be firstly collected respectively after lysis of cells or tissues, followed by preparing a nano-vaccine or micron-vaccine respectively; or the cells or tissues is lysed directly with a solubilizing solution containing a solubilizer, and then the whole-cell components is solubilized with such solubilizing solution containing a solubilizer, followed by preparing a nano-vaccine or micron-vaccine.

The method for preparing a targeting delivery system (also referred to as a nano-vaccine or a micron-vaccine) described in the present invention is a conventional preparation method. In some embodiments, the preparation of the nano-vaccine or micron-vaccine adopts a double-emulsion of the solvent evaporation, and the material for preparing the nanoparticles or micron-particles are organic polymer of poly(lactic-co-glycolic acid) copolymer (PLGA) and poly-lactic acid (PLA). The immune adjuvants used in preparation are poly(I:C), Bacille Calmette-Guerin (BCG) or CpG. Those skilled in the art can understand that in practice, they can appropriately modify the preparation method, preparation process, preparation materials for the nanoparticles or micron-particles, types and concentrations of the immune adjuvants, etc. according to specific condition.

In some embodiments, the specific preparation method of the double-emulsion method used in the present invention is as follows:

Step 1, adding the first predetermined volume of aqueous phase solution containing the first predetermined concentration to the second predetermined volume of organic phase of the medical polymer material containing the second predetermined concentration.

In some embodiments, the aqueous phase solution contains each component in cancer cells lysate and immune enhancing adjuvants, such as poly(I:C), BCG or CpG; each component in the cancer cells lysate were water-soluble components or original water-insoluble components solubilized with 8 M urea or other solubilizer, respectively. The concentration of the water-soluble components from cancer cells or the original water-insoluble components from cancer cells solubilized with 8 M urea contained in the aqueous phase solution, that is, the first predetermined concentration, requires that the concentration of the proteins and peptides are larger than 1 ng/mL. The reason for selecting such concentration is that through a large number of experiments, the inventors found that, generally, the higher the concentration of the aqueous solution of cancer cells lysate used, the more the various types of cancer antigens are loaded onto the prepared nanoparticles or micron-particles. When the prepared proteins and peptides have a concentration larger than 1 ng/mL, that is, the first predetermined concentration is larger than 1 ng/mL, enough cancer antigens can be loaded to activate relevant immune response. The concentration of the immune enhancing adjuvants in the initial aqueous phase was larger than 0.01 ng/mL. Additionally, the first predetermined volume is 600 μL.

In some embodiments, the aqueous phase solution contains each component in tumor tissues lysate and immune enhancing adjuvants, such as poly(I:C), BCG or CpG; each component in the tumor tissues lysate was water-soluble components or original water-insoluble components solubilized with 8 M urea or other solubilizer, respectively. The concentration of the water-soluble components from tumor tissues or the original water-insoluble components from tumor tissues solubilized with 8 M urea contained in the aqueous phase solution, that is, the first predetermined concentration, requires that the concentration of the proteins and peptides is larger than 1 ng/mL. The reason for selecting such concentration is that through a large number of experiments, the inventors found that, common the higher the concentration of the aqueous solution of tissues lysate used, the more the various types of cancer antigens are loaded onto the prepared nanoparticles or micron-particles. When the prepared protein and peptide has a concentration larger than 1 ng/mL, that is, the first predetermined concentration is larger than 1 ng/mL, enough cancer antigens can be loaded to activate relevant immune response. The concentration of the immune adjuvants in the initial aqueous phase is larger than 0.01 ng/mL. Additionally, the first predetermined volume is 600 μL.

In the present invention, solubilizing the medical polymer material in the organic solvent to obtain the organic phase with a second the predetermined volume containing the medical polymer material of with the second predetermined concentration. In some embodiments, the medical polymer material is a mixture of target head-modified PLGA, PLGA and PLA, and the organic solvent is dichloromethane. The volume of the obtained organic phase, that is, the second predetermined volume is 2 mL. In addition, in some embodiments, the range of the second predetermined concentration of the medical polymer materials is 0.5 mg/mL-5000 mg/mL, preferably 100 mg/mL.

In the present invention, PLGA and targeting head-modified PLGA are chosen because it is a biodegradable materials and has been approved by the FDA for use as a pharmaceutical adjuvants. In practice, we can apply any other mixture of target-modified materials and materials, that can be used to prepare nano-sized particles or micron-sized particles.

In practice, the second predetermined volume of the organic phase is set according to its ratio to the first predetermined volume of the aqueous phase. In the present invention, the range of the ratio of the first predetermined volume of the aqueous phase to the second predetermined volume of the organic phase is 1:1.1 to 1:5000, preferably 1:10. In specific process, the first predetermined volume, the second predetermined volume and the ratio of the first predetermined volume to the second predetermined volume can be adjusted according to the need in order to adjust the size of the prepared nanoparticles or micron-particles.

Step 2, the mixture obtained in step 1 is treated with sonication for larger than 2 seconds or stirring for larger than 1 minute.

This step is for nanometerization or micronization. The duration of the sonication or the speed and duration of the stirring can control the size of the prepared nanoparticles, while the duration is too long or too short will result in the change of particles size. For this reason, it is necessary to choose proper sonication duration. In the present invention, the duration of the sonication is larger than 2 seconds, the stirring speed is larger than 50 rpm, and the stirring duration is larger than 1 minute.

Step 3, the mixture obtained after the treatment in step 2 is added into the third predetermined volume of emulsifier aqueous solution containing third predetermined concentration, followed by sonication treatment for larger than 2 seconds or stirring for larger than 1 minute.

In this step, the mixture obtained in step 2 is added into the emulsifier aqueous solution to continue sonication or stirring for nanometerization or micronization.

In the present invention, the emulsifier aqueous solution is a polyvinyl alcohol (PVA) aqueous solution, the third predetermined volume is 5 mL, and the third predetermined concentration is 20 mg/mL. The third predetermined volume is adjusted according to its ratio to the second predetermined volume. In the present invention, the ratio of the second predetermined volume to the third predetermined volume is set in the range of 1:1.1 to 1:1000, preferably 2:5. In specific process, in order to control the size of the nanoparticles, the ratio of the second predetermined volume to the third predetermined volume can be adjusted.

Similarly, in this step, the selection of the duration of sonication or stirring, the selection of the volume and concentration of the emulsifier aqueous solution are all based on obtaining nanoparticles or micron-particles with proper size.

Step 4, the liquid, obtained after the treatment in step 3, is added into an emulsifier aqueous solution with the fourth predetermined volume and the fourth predetermined concentration, followed by stirring until in accordance with the predetermined stirring condition.

In this step, the emulsifier aqueous solution is still PVA, and the fourth predetermined volume is larger than 50 mL. The fourth predetermined concentration is 5 mg/mL. The selection of the fourth predetermined concentration is based on obtaining nanoparticles or micron-particles with proper size. The selection of the fourth predetermined volume is determined according to the ratio of the third predetermined volume to the fourth predetermined volume. In the present invention, the range of the ratio of the third predetermined volume to the fourth predetermined volume is 1:1.5-1:2000, preferably 1:10. In specific process, the ratio of the third predetermined volume to the fourth predetermined volume may be adjusted to control the size of the nanoparticles or micron-particles.

In the present invention, the predetermined stirring condition in this step is until the complete evaporation of the organic solvent, that is, the complete evaporation of the dichloromethane in step 1.

Step 5, the mixture, obtained in step 4 in accordance with the predetermined stirring condition, is centrifuged for larger than 1 minute at a rotating speed larger than 100 RPM. The supernatant was removed and the remaining precipitation was resuspended in aqueous solution containing a lyoprotectant with the fifth predetermined volume and the fifth predetermined concentration or PBS (or physiological saline solution) with the sixth predetermined volume.

In some embodiments of the present invention, the precipitation obtained in step 5 does not need to be lyophilized when resuspended in PBS (or physiological saline solution) with the sixth predetermined volume, and can be used directly in subsequent experiments related to the adsorption of cancer cells lysates onto the surface of nanoparticles or micron-particles.

In some embodiments of the present invention, the precipitation obtained in step 5 needs to be lyophilized when resuspended in the aqueous solution containing a lyoprotectant, then can be used in subsequent experiments related to the adsorption of cancer cells lysates onto the surface of nanoparticles or micron-particles after lyophilization.

In the present invention, trehalose is selected as the lyoprotectant.

In the present invention, the fifth predetermined volume of the lyoprotectant in this step is 20 mL, and the fifth predetermined concentration is 4% by mass percentage. The reason for this setting is to avoid affecting the lyophilization effect in subsequent lyophilization.

Step 6, the suspension containing the lyoprotectant obtained in step 5 is lyophilized, and the lyophilized substance obtained in step 5 is for subsequent use.

Step 7, a nano-vaccine or micron-vaccine is obtained by mixing the nanoparticles-containing (or micron-particles-containing) suspension obtained in step 5 by resuspending in PBS (or physiological saline solution) with the sixth predetermined volume or the lyophilized substance obtained in step 6 (containing nanoparticles or micron-particles and lyoprotectant after lyophilization) resuspending with PBS (or physiological saline solution) with the sixth predetermined volume, and the water-soluble components with the seventh predetermined volume or the original water-insoluble components solubilized with 8 M urea, followed by standing for larger than 0.1 minute.

In the present invention, the volume ratio of the sixth predetermined volume to the seventh predetermined volume is 1:10000 to 10000:1, preferred volume ratio is 1:100 to 100:1, and the most preferred volume ratio is 1:30 to 30:1.

In some embodiments, the volume of the suspension containing resuspended nanoparticles or micron-particles are 10 mL. The volume of the water-soluble components or the original water-insoluble components solubilized with 8 M urea containing the cancer cells lysate or the tumor tissues lysate is 1 mL.

Figure 2:
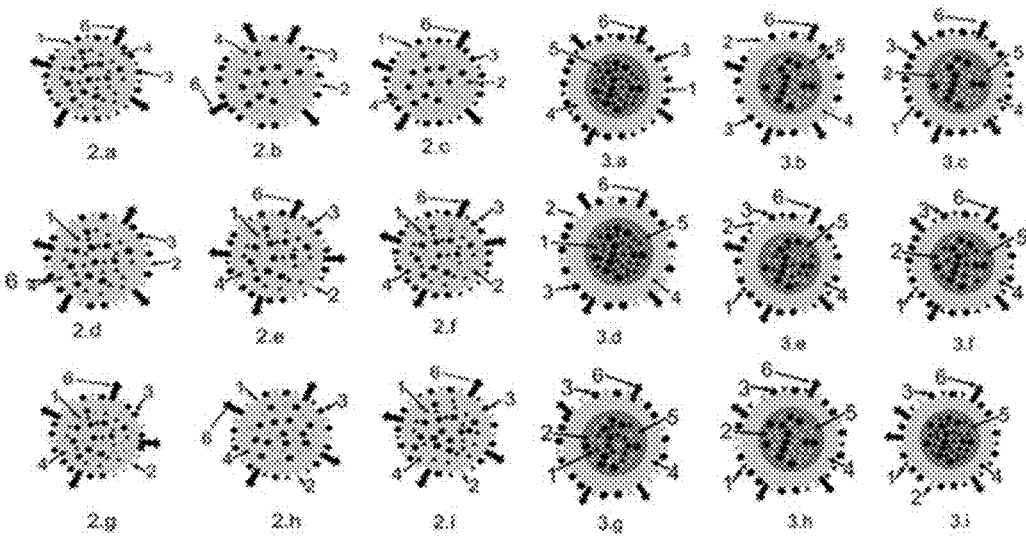
FIG. 2-FIG. 12 are schematic diagrams of the structure of nanoparticles or micron-particles loaded with water-soluble and water-insoluble cells components, wherein 1, water-soluble components of cells or tissues; 2, water-insoluble components of cells or tissues; 3, immune adjuvants; 4, nanoparticles or micron-particles; 5, the inner core of a nanoparticles; 6, targeting head that can target specific cells or tissues.
Figures 3, 4:
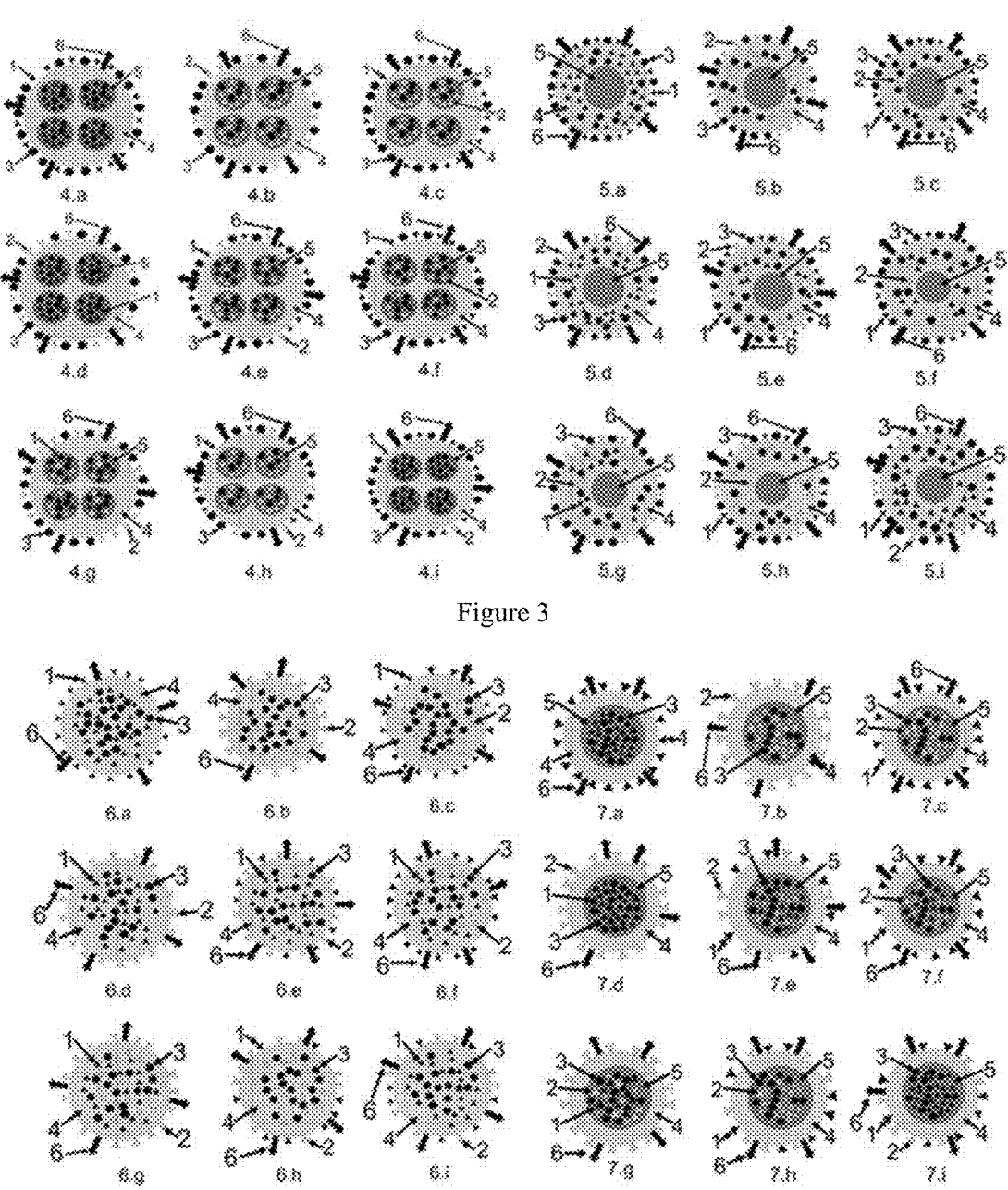
Figure 5:
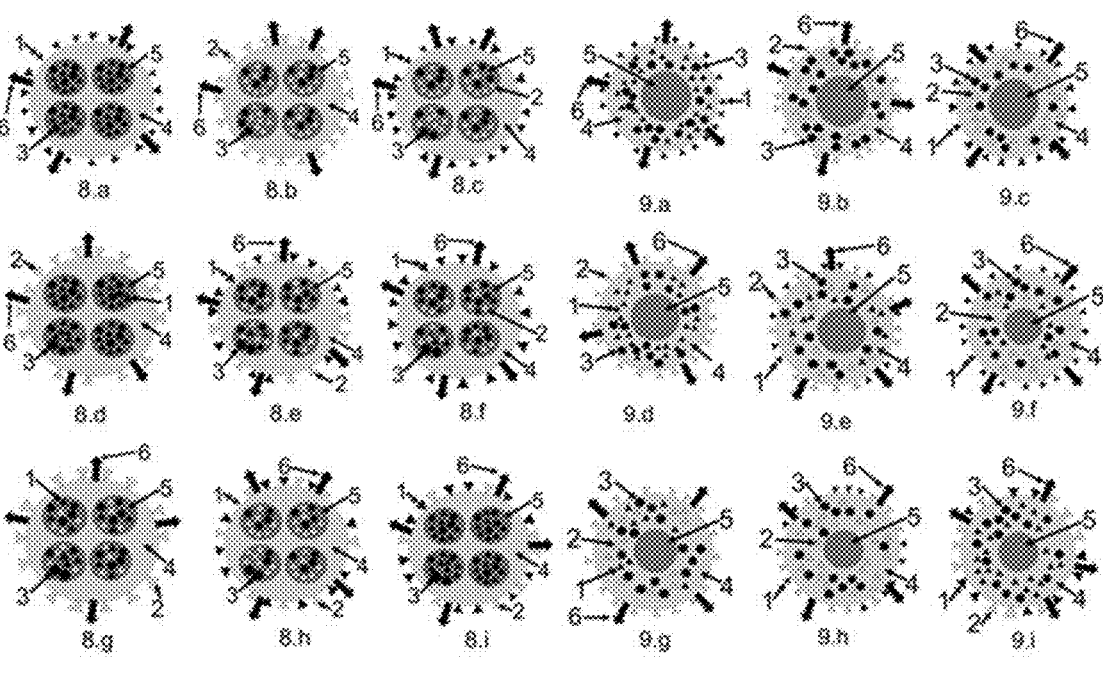
Figure 6:
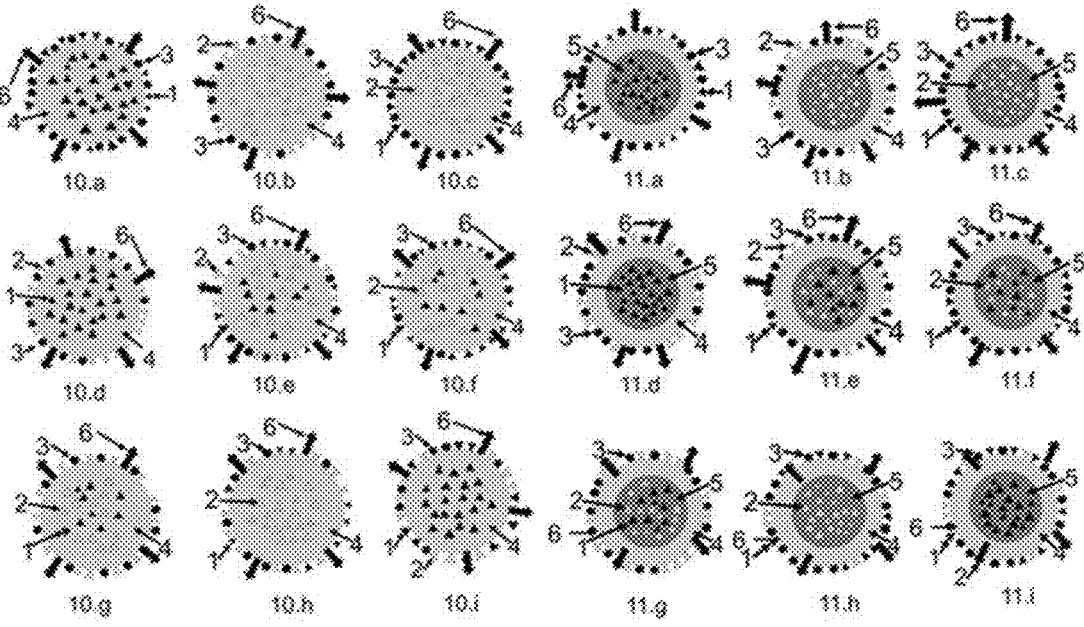
Figure 7:
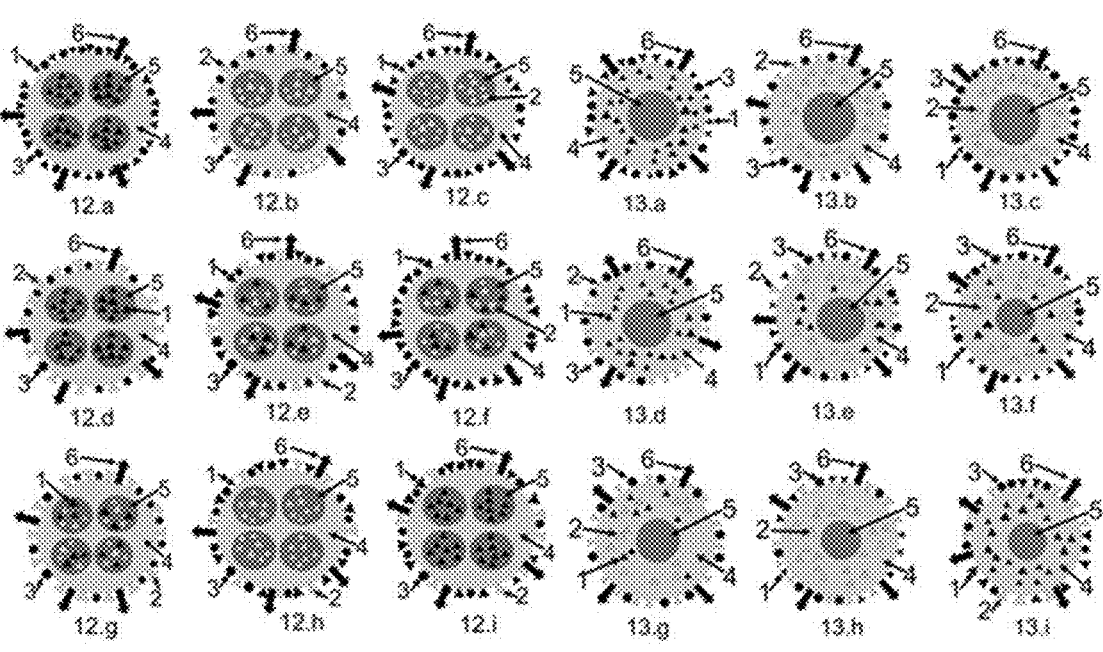
Figure 8:
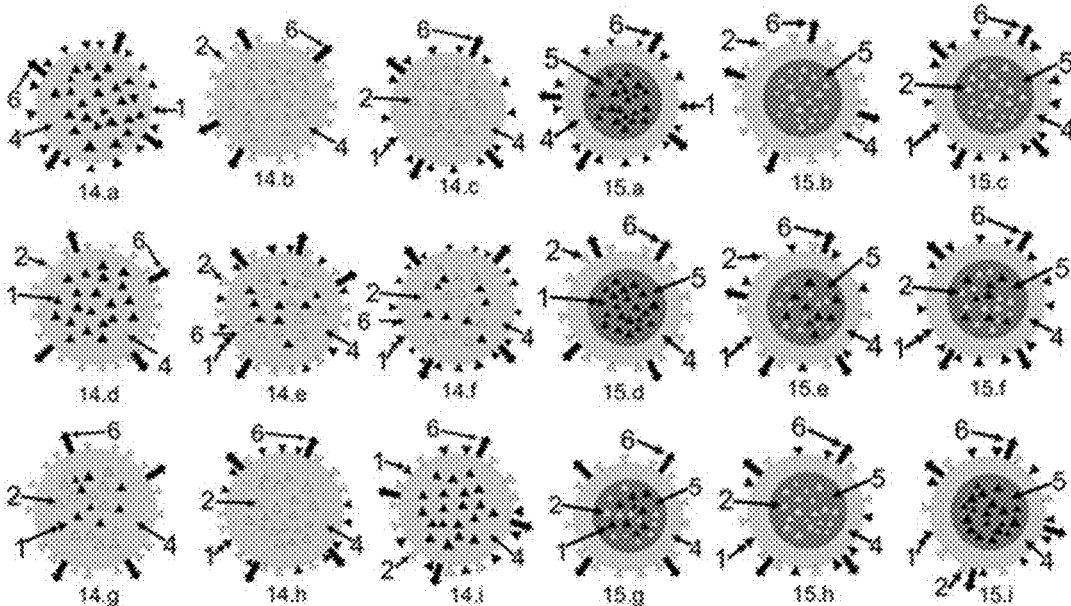
Figure 9:
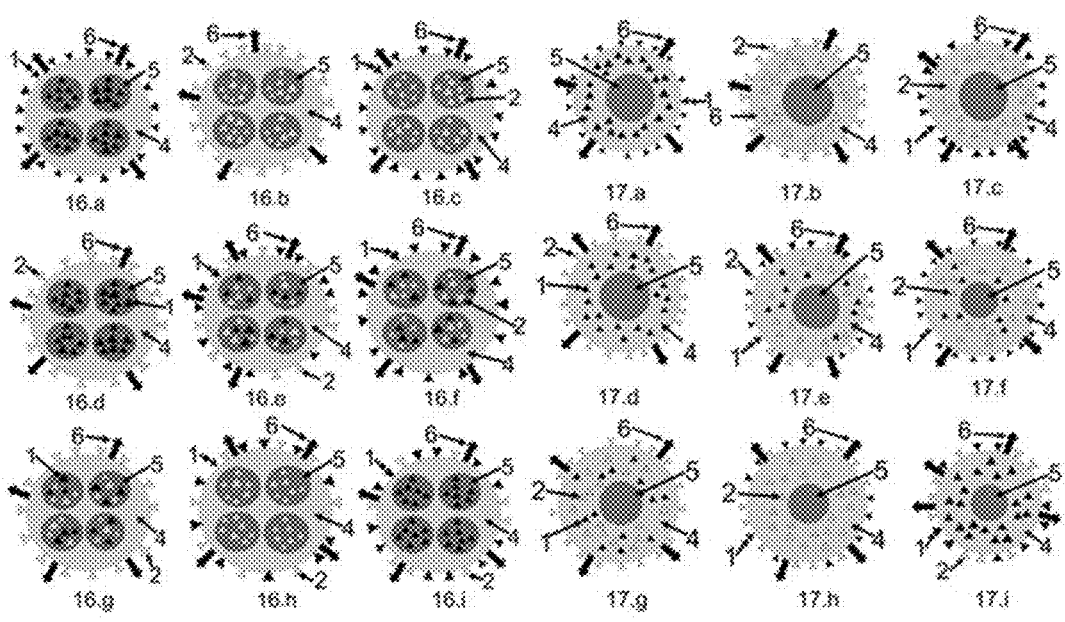

In some embodiments, as shown in FIG. 2, in the present invention, the water-soluble portion of the cell components that is soluble in pure water or (and) the water-insoluble portion of the cell components solubilized with a solubilizer was loaded onto nanoparticles or micron-particles, together with the immune enhancing adjuvants; and then, the water-soluble portion or (and) the water-insoluble portion of the cell components was adsorbed onto the surface of the nanoparticles or micron-particles, together with the immune enhancing adjuvants. Therefore, the loading capacity of the nanoparticles or micron-particles for the water-soluble or water-insoluble components of the cells can be maximized. In practice, a solubilizing solution containing a solubilizer (such as 8 M urea aqueous solution or 6 M guanidine hydrochloride aqueous solution) can also be used to directly lyse cells or tissues and then directly solubilize whole-cell components, followed by preparing nano-vaccine or micron-vaccine with the obtained substances.

The following is a further description of a targeting delivery system loaded with whole-cell components provided by the present invention and use thereof.

Example 1: Mannose-Modified Nanoparticles Loaded with Whole-Cell Components of Melanoma Tumor Tissues Inside Thereof for Cancer Treatment This example uses mouse melanoma as a cancer model to illustrate how to prepare a nano-vaccine loaded with whole-cell components of tumor tissues for the treatment of melanoma. In practice, the detailed dosage form, adjuvants, administration time, administration frequency, and dosage regimen can be adjusted accordingly.

In this example, B16-F10 mouse melanoma was used as a cancer model. In this example, the lysed components of mouse melanoma tumor tissues were loaded inside and onto the surface of nanoparticles to prepare nano-vaccine. Mouse melanoma tumor masses were first obtained and lysed to prepare the water-soluble components and the original water-insoluble components solubilized with 8 M urea of tumor mass tissues. Then, a nano-vaccine loaded with water-soluble and water-insoluble components of tumor tissues lysate was prepared by using solvent evaporation method, with PLGA (50:50) and PLA as nanoparticles backbone materials, and CpG as immune adjuvants. The nano-vaccine then for use in treating tumors in melanoma tumor-bearing mice.

(1) Lysis of Tumor Tissues and Collection of Components 150,000 B16-F10 melanoma cells were subcutaneously inoculated on the back of each C57BL/6 mouse, and the mice were euthanatized when the inoculated tumors in each mouse grew to a volume of 400 mm$^3$ to 1500 mm$^3$, followed by harvesting the tumor tissues. The tumor tissues was cut into pieces and ground, filtered through a cell strainer and added with an appropriate amount of pure water, followed by repeated freeze-thawing and sonication for at least 5 times. After the cells of the tumor tissues were lysed, the cell lysate of the tumor tissues was centrifuged at a speed of larger than 12,000 RPM for 5 min, and the supernatant was obtained as the water-soluble components of the tumor tissues that was soluble in pure water; 8 M urea aqueous solution was added into solubilizing the precipitation portion and the original water-insoluble components that are insoluble in pure water were converted to be soluble in 8 M urea aqueous solution. The above obtained water-soluble components and the original water-insoluble components, solubilized with 8 M urea, of the tumor tissues lysate were original material sources for preparing the nano-vaccine to treat cancer.

(2) Preparation of Nano-Vaccine

In this example, the nano-vaccine and the blank nanoparticles using as control were prepared by double emulsion of solvent evaporation. The preparation materials of nanoparticles were using PLGA (50:50) with the molecular weight of 24 KDa-38 KDa, the mannose modified PLGA (50:50) with the molecular weight of 24 KDa-38 KDa and the PLA with the molecular weight of 10 KDa. The mass ratio of unmodified PLGA, mannose-modified PLGA and PLA was 8:1:2. The immune adjuvants used was CpG and CpG was distributed inside the nanoparticles. The preparation method was as described above. The average particle size of the nanoparticles was about 280 nm, and the average surface potential Zeta potential of the nanoparticles was about −8 mV. Each 1 mg PLGA nanoparticles loaded with 60 μg of proteins or peptides components and the immune adjuvants CpG used for each 1 mg PLGA nanoparticles are 0.01 mg, with half inside and half outside. Blank nanoparticles with a particle size of about 240 nm were prepared by using pure water or 8 M urea containing equal amount of CpG to replace the corresponding water-soluble components and water-insoluble components, respectively.

(3) Nano-Vaccine for Cancer Treatment

The experimental groups used in this study were as follows: nano-vaccine group, PBS control group, blank nanoparticles+tissues lysate group.

Female C57BL/6 mice aged 6-8 weeks were selected as model mice for the preparation of melanoma-bearing mice.

The dosage regimen of nano-vaccine group was as follows: 150,000 B16-F10 cells were inoculated subcutaneously on the lower right side of the back of each mouse on day 0. 200 μL of 2 mg PLGA nanoparticles loaded with the water-soluble components of the cancer cells lysate both inside and onto the surface, and 200 μL of 2 mg PLGA nanoparticles loaded with the original water-insoluble components, solubilized with 8 M urea both inside and onto the surface were subcutaneously administered on day 4, day 7, day 10, day 15 and day 20, respectively.

The dosage regimen of the PBS blank control group was as follows: 150,000 B16-F10 cells were inoculated subcutaneously on the lower right side of the back of each mouse on day 0, and 400 μL of PBS was injected subcutaneously on day 4, day 7, day 10, day 15 and day 20, respectively.

Blank nanoparticles+tissues lysate control group: 150,000 B16-F10 cells were inoculated subcutaneously on the lower right side of the back of each mouse on day 0. Equal amounts of water-soluble components of tumor tissues lysate, equal amounts of the original water-insoluble components of lysate solubilized with 8 M urea and 4 mg of PLGA blank nanoparticles, loaded with equal amounts of CpG without any lysate components, were injected subcutaneously on day 4, day 7, day 10, day 15 and day 20, respectively. It should be noted that the above three injections should be administered separately and injected at different sites to avoid adsorption of the free lysate onto the surface of the blank nanoparticles.

During the experiment, the size of the tumor volume of the mice was recorded every three days from day 6 onwards. The tumor volume was calculated using the formula $v=0.52*a*b^2$, wherein v is the tumor volume, a is the tumor length and b is the tumor width.

For ethical reasons of animal experiment, a mouse was considered dead and euthanized when its tumor volume exceeded 2000 mm³ in the survival time experiment.

(4) Experimental Results

Figure 13:
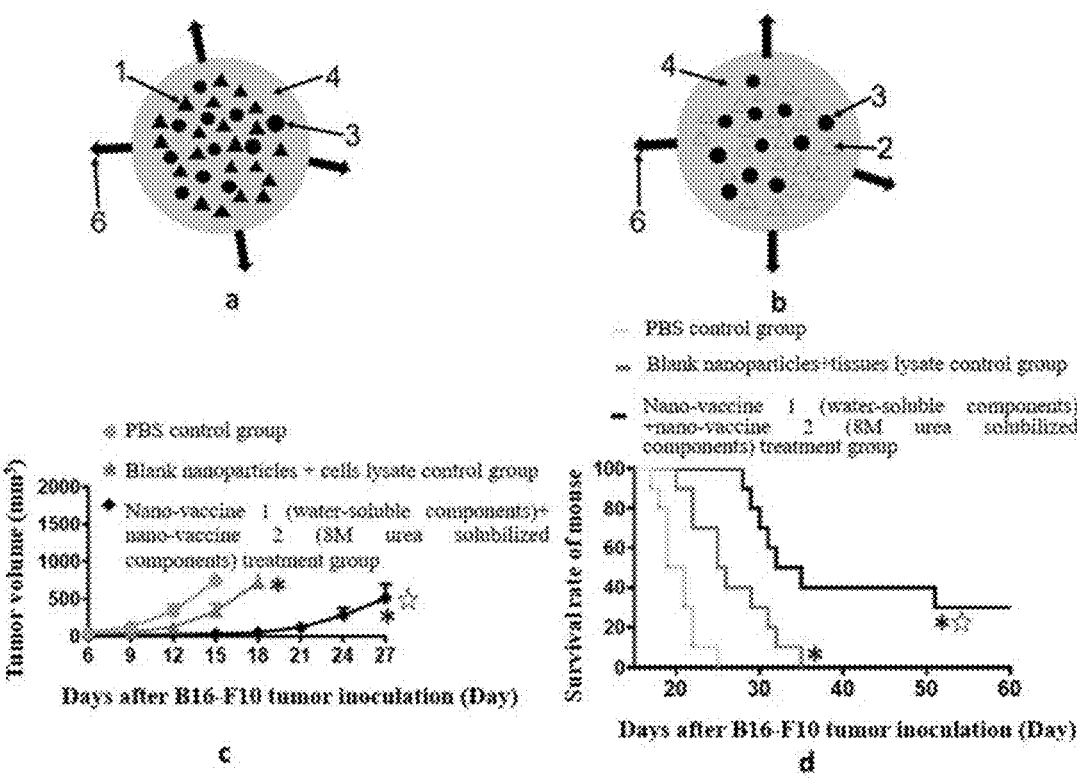

As shown in FIG. 13, compared with the PBS blank control group and the blank nanoparticles+tissues lysate control group, the tumor growth rate of the mice in the nano-vaccine group was significantly slower (p<0.05) and the survival time of the mice was significantly prolonged (p<0.05). This shows that the nano-vaccine loaded with water-soluble and water-insoluble components of cancer cells has a therapeutic effect on melanoma and can partially cure melanoma.

Example 2: Mannose-Modified Micron-Particles Loaded with Whole-Cell Components of Melanoma Tumor Tissues Both Inside and onto the Surface Thereof for Cancer Treatment This example uses B16-F10 mouse melanoma as cancer model to illustrate how to treat melanoma with micron-vaccine. In practice, the specific dosage form can be adjusted according to the situation.

In this example, all the lysed components of mouse melanoma tumor tissues were loaded both inside and onto the surface of micron-particles to prepare micron-vaccine. Mouse melanoma tumor masses were first obtained and lysed to prepare the water-soluble components and the original water-insoluble components solubilized with 8 M urea of tumor mass tissues. Then, a micron-vaccine loaded with water-soluble and water-insoluble components of tumor tissues lysate was prepared, using PLGA (50:50) as micron-particles backbone materials and poly(I:C) as immune adjuvants, by solvent evaporation method. The micron-vaccine then for use in treating tumors in melanoma tumor-bearing mice.

(1) Lysis of Tumor Tissues and Collection of Components

The treatment method is the same as that of Example 1.

(2) Preparation of Micron-Vaccine

In this example, the micron-vaccine and the blank micron-particles as control were prepared using double emulsion method of solvent evaporation method. The micron-particles were prepared using PLGA (50:50) with a molecular weight of 24 KDa-38 KDa, and the mannose modified PLGA (50:50) with the molecular weight of 24 KDa-38 KDa. The mass ratio of unmodified PLGA and mannose-modified PLGA was 10:1. The immune adjuvants used was poly(I:C) and poly(I:C) was distributed inside the micron-particles. The preparation method was as described above, and the water-soluble components and the water-insoluble components are together loaded onto the same micron-particles. In this example, whole-cell components were loaded both inside and onto the surface of the micron-particles. To load the whole-cell components onto the surface of the micron-particles, the micron-particles, already loaded with the whole-cell components, were mixed with the cell components at a volume ratio of 10:1, followed by standing for 15 minutes. The average particle size of micron-particles was about 2.0 and the average surface potential Zeta potential of micron-particles was about −17 mV. Each 1 mg PLGA micron-particles was loaded with 70 μg of proteins or peptides components, and the immune adjuvant poly(I:C) used for each 1 mg PLGA micron-particles was 0.01 mg, with half inside and half outside. Blank micron-particles with a particle size of about 1.8 μm were prepared by using pure water or 8 M Urea Containing Equal Amount of Poly(I:C) to Replace corresponding water-soluble components and water-insoluble components, respectively.

(3) Micron-Vaccine for Cancer Treatment

The experimental groups in this study were as follows: micron-vaccine group; PBS control group, blank micron-particles+cells lysate group. Female C57BL/6 mice aged 6-8 weeks were selected as model mice for the preparation of melanoma-bearing mice.

The dosage regimen of micron-vaccine group was as follows: 150,000 B16-F10 cells were inoculated subcutaneously on the lower right side of the back of each mouse on day 0, and 400 μL of 4 mg PLGA micron-vaccines, loaded with the water-soluble components and water-insoluble components of the cancer cells lysate both inside and onto the surface of micron-vaccines, were subcutaneously administered on day 4, day 7, day 10, day 15 and day 20, respectively.

The dosage regimen of the PBS blank control group was as follows: 150,000 B16-F10 cells were inoculated subcutaneously on the lower right side of the back of each mouse on day 0, and 400 μL of PBS was injected subcutaneously on day 4, day 7, day 10, day 15 and day 20.

Blank micron-particles+cells lysate control group: 150,000 B16-F10 cells were inoculated subcutaneously on the lower right side of the back of each mouse on day 0. Equal amounts of water-soluble and water-insoluble components of cancer cells lysate and 4 mg of PLGA blank nanoparticles loaded with equal amounts of poly(I:C) without any lysate components were injected subcutaneously on day 4, day 7, day 10, day 15 and day 20, respectively. It should be noted that the above two injections should be administered separately and injected at different sites to avoid adsorption of the free cell lysate onto the surface of the blank nanoparticles.

In the experiment, the size of the tumor volume of the mice was recorded every three days from day 6 onwards. The tumor volume was calculated using the formula $v=0.52*a*b^2$, wherein v is the tumor volume, a is the tumor length and b is the tumor width.

(4) Experimental Results

Figure 14:
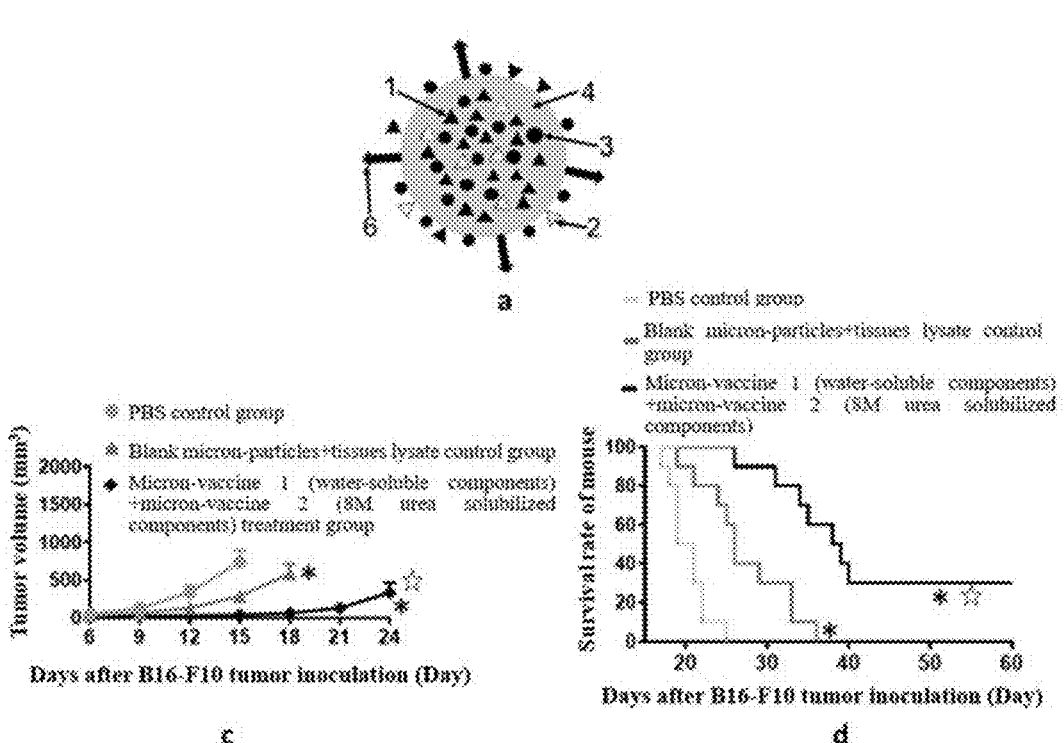

As shown in FIG. 14, compared with the PBS blank control group and the blank micron-particles+cells lysate control group, the tumor growth rate of the mice in the micron-vaccine group was significantly slower (p<0.05) and the survival time of the mice was significantly prolonged (p<0.05). This shows that the micron-vaccine loaded with water-soluble and water-insoluble components of cancer cells has a therapeutic effect on melanoma and can partially cure melanoma.

Example 3 Mannose-Modified Nanoparticles Loaded with Whole-Cell Components of Melanoma Tumor Tissues Both Inside and onto the Surface Thereof for Cancer Prevention This example uses melanoma mouse as cancer model to illustrate how to prepare nano-vaccines loaded with whole-cell components of tumor tissues and apply such nano-vaccines to prevent melanoma. In practice, the detailed dosage form, adjuvants, administration time, administration frequency, and dosage regimen can be adjusted according to the situation.

In this example, B16-F10 melanoma mouse was used as a cancer model. In this example, the lysed components of melanoma mouse tumor tissues were loaded inside and onto the surface of nanoparticles to prepare nano-vaccine. Mouse melanoma tumor masses were first obtained and lysed to prepare the water-soluble components and the original water-insoluble components solubilized with 8 M urea of tumor mass tissues. Then, a nano-vaccine loaded with water-soluble and water-insoluble components of tumor tissues lysate was prepared, using PLGA (50:50) as nanoparticles backbone materials and poly(I:C) as immune adjuvants, by solvent evaporation method. The nano-vaccine was then used to prevent tumors in melanoma tumor-bearing mice.

(1) Lysis of Tumor Tissues and Collection of Components

The method is the same as that of Example 1.

(2) Preparation of Nano-Vaccine

In this example, the nano-vaccine and the blank nanoparticles as control were prepared using double emulsion method of the solvent evaporation method. The nanoparticles were prepared using PLGA with a molecular weight of 24 KDa-38 Kda, and the mannose modified PLGA with a molecular weight of 24 KDa-38 KDa. The mass ratio of unmodified PLGA and mannose-modified PLGA was 10:1. The immune adjuvants used were poly(I:C) and poly(I:C) was distributed inside the nanoparticles. The preparation method was as described above, the difference is that in this example, whole-cell components were loaded together both inside and onto surface of the nanoparticles. To load the whole-cell components onto the surface of the nanoparticles, the nanoparticles, already loaded with the whole-cell components, were mixed with the cell components at a volume ratio of 10:1, followed by standing for 15 minutes. The average particle size of nanoparticles was about 300 nm, and the average surface potential Zeta potential of nanoparticles was about −8 mV. Each 1 mg PLGA nanoparticles loaded with 60 μg of proteins or peptides components, and the immune adjuvants poly(I:C) used for each 1 mg PLGA was 0.01 mg, with half inside and half outside. Blank nanoparticles with a particle size of about 260 nm were prepared by using pure water or 8 M urea containing equal amount of poly(I:C) to replace corresponding water-soluble components and water-insoluble components, respectively.

(3) Nano-Vaccine for Cancer Prevention

Female C57BL/6 mice aged 6-8 weeks were selected as model mice for the preparation of melanoma-bearing mice. 200 μL of 2 mg PLGA nano-vaccine, loaded with the water-soluble components of the cancer cells lysate both inside and onto the surface, and 200 μL of 2 mg PLGA nano-vaccine, loaded with the original water-insoluble components solubilized with 8 M urea both inside and onto the surface, were subcutaneously administered on day 42, day 35, day 10, day 15 and day 20, before the inoculation of B16-F10 cancer cells, respectively. 14 days after the last nano-vaccine injection, 150,000 B16-F10 cells were inoculated subcutaneously on the lower right side of the back of each mouse, and that day was set as day 0 of cancer cells inoculation. In this experiment, the regimen of PBS blank control was as follows: 400 μL of PBS was injected subcutaneously on day 42, day 35, day 28, day 21, and day 14 before inoculation of B16-F10 cancer cells. 150,000 B16-F10 cells were inoculated subcutaneously on the lower right side of the back of each mouse on day 0.

In the experiment, the size of the tumor volume of the mice was recorded every three days from day 6 onwards. The tumor volume was calculated using the formula $v=0.52*a*b^2$, wherein v is the tumor volume, a is the tumor length and b is the tumor width.

(4) Experimental Results

Figure 15:
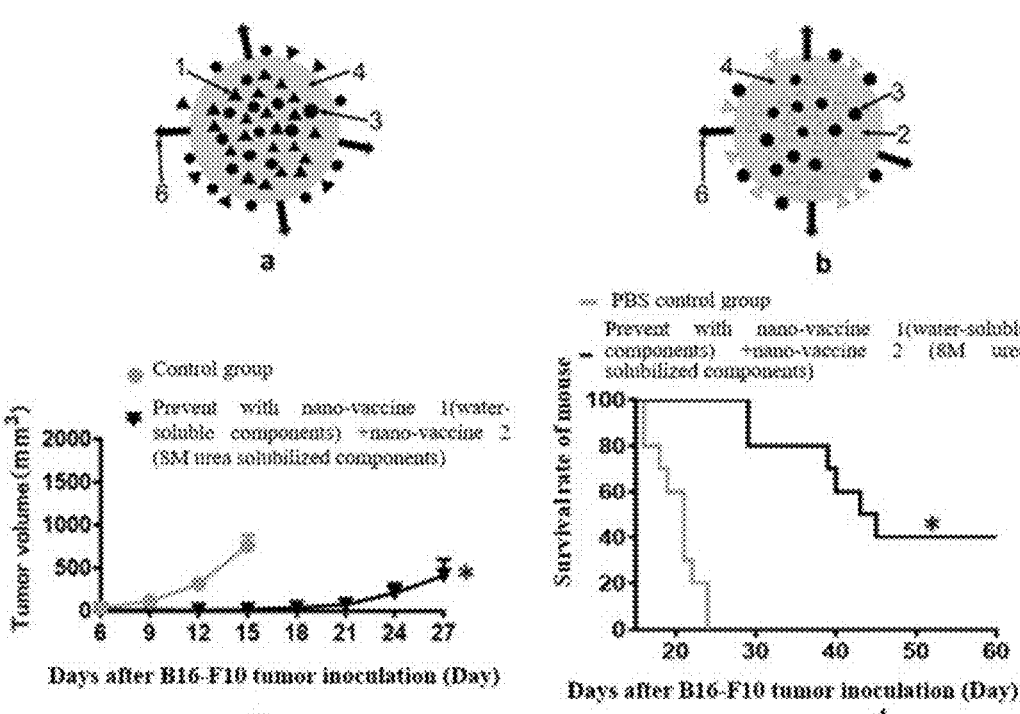

As shown in FIG. 15, compared with the PBS blank control group, the tumor growth rate of the mice in the nano-vaccine group was significantly slower (p<0.05) and the survival time of the mice was significantly prolonged (p<0.05). This shows that the nano-vaccine with targeting ability to dendritic cell, loaded with water-soluble components and water-insoluble components of cancer cells, has a prevention effect on melanoma.

Example 4: Mannose-Modified Nanoparticles Loaded with Whole-Cell Components of Lung Cancer Tumor Tissues Inside Thereof for the Prevention of Lung Cancer This example uses mouse with lung cancer as a cancer model to illustrate how to prepare nano-vaccine loaded with whole-cell components of tumor tissues and apply such nano-vaccine to prevent lung cancer. In practice, the detailed dosage form, adjuvants, administration time, administration frequency, and dosage regimen can be adjusted according to the situation.

In this example, LLC lung cancer mouse was used as a cancer model. In this example, the lysed components of mouse lung cancer tumor tissues were loaded inside and onto the surface of nanoparticles to prepare nano-vaccine. First, tumor masses from lung cancer mice were obtained and lysed to prepare the water-soluble components and the original water-insoluble components solubilized with 8 M urea of tumor mass tissues. Then, nano-vaccine loaded with water-soluble and water-insoluble components of tumor tissues lysate was prepared, using PLGA (50:50) as nanoparticles backbone materials and poly(I:C) as immune adjuvants, by solvent evaporation method. The nano-vaccine then was used to prevent tumors in tumor-bearing mice with lung cancer.

(1) Lysis of Tumor Tissues and Collection of Components 1000,000 LLC cells were subcutaneously inoculated at the lateral abdomen of each C57BL/6 mouse, and the mice were euthanatized when the inoculated tumors in each mouse grew to a volume of 400 mm³ to 1500 mm³, followed by harvesting the tumor tissues. The tumor tissues was cut into pieces, ground, and filtered through a cell strainer, and added with an appropriate amount of pure water, followed by repeated freeze-thawing and sonication at least 5 times. After the cells of the tumor tissues were lysed, the cell lysate of the tumor tissues was centrifuged at a speed of larger than 12,000 RPM for 5 min, and the supernatant was obtained as the water-soluble components in the tumor tissues that was soluble in pure water; addition of 8 M urea aqueous solution to solubilize the precipitation portion can convert the original water-insoluble components in pure water to being soluble in 8 M urea solution. The above obtained water-soluble components and the original water-insoluble components solubilized with 8 M urea of the tumor tissues lysate were original material sources for preparing the nano-vaccine to prevent cancer.

(2) Preparation of Nano-Vaccine

In this example, the nano-vaccine and the blank nanoparticles as control were prepared by double emulsion method of solvent evaporation method. The nanoparticles were prepared using PLGA with a molecular weight of 24 KDa-38 KDa and the mannose modified PLGA with a molecular weight of 24 KDa-38 KDa. The mass ratio of unmodified PLGA and mannose-modified PLGA was 10:1. The immune adjuvants used were poly(I:C) and poly(I:C) was distributed inside the nanoparticles. The preparation method is as described above. The average particle size of nanoparticles was about 300 nm, and the average surface potential Zeta potential of nanoparticles was about −8 mV. Each 1 mg PLGA nanoparticles loaded with 60 μg of proteins or peptides components, and the immune adjuvants poly(I:C) used for each 1 mg PLGA nanoparticles was 0.01 mg, with half inside and half outside. Blank nanoparticles with a particle size of about 260 nm were prepared by using pure water or 8 M urea containing equal amount of poly(I:C) to replace corresponding water-soluble components and water-insoluble components, respectively.

(3) Nano-Vaccine for Lung Cancer Prevention

Female C57BL/6 mice aged 6-8 weeks were selected as model mice for the preparation of lung cancer-bearing mice.

The dosage regimen of nano-vaccine group was as follows: 200 μL of 2 mg PLGA nanoparticles loaded with the water-soluble components of the cancer cells lysate both inside and onto the surface, and 200 μL of 2 mg PLGA nanoparticles loaded with the original water-insoluble components solubilized with 8 M urea both inside and onto the surface were subcutaneously administered on day −49, day −42, day −35, day −28 and day −14, before the inoculation of cancer cells, respectively. The PBS control group was injected with 400 μL PBS on the corresponding days. 1,000,000 LLC lung cancer cells were inoculated subcutaneously on the lower right back of each mouse on day 0.

In the experiment, the size of the tumor volume of the mice was recorded every three days from day 6 onwards. The tumor volume was calculated using the formula $v=0.52*a*b^2$, wherein v is the tumor volume, a is the tumor length and b is the tumor width.

(4) Experimental Results

Figure 16:
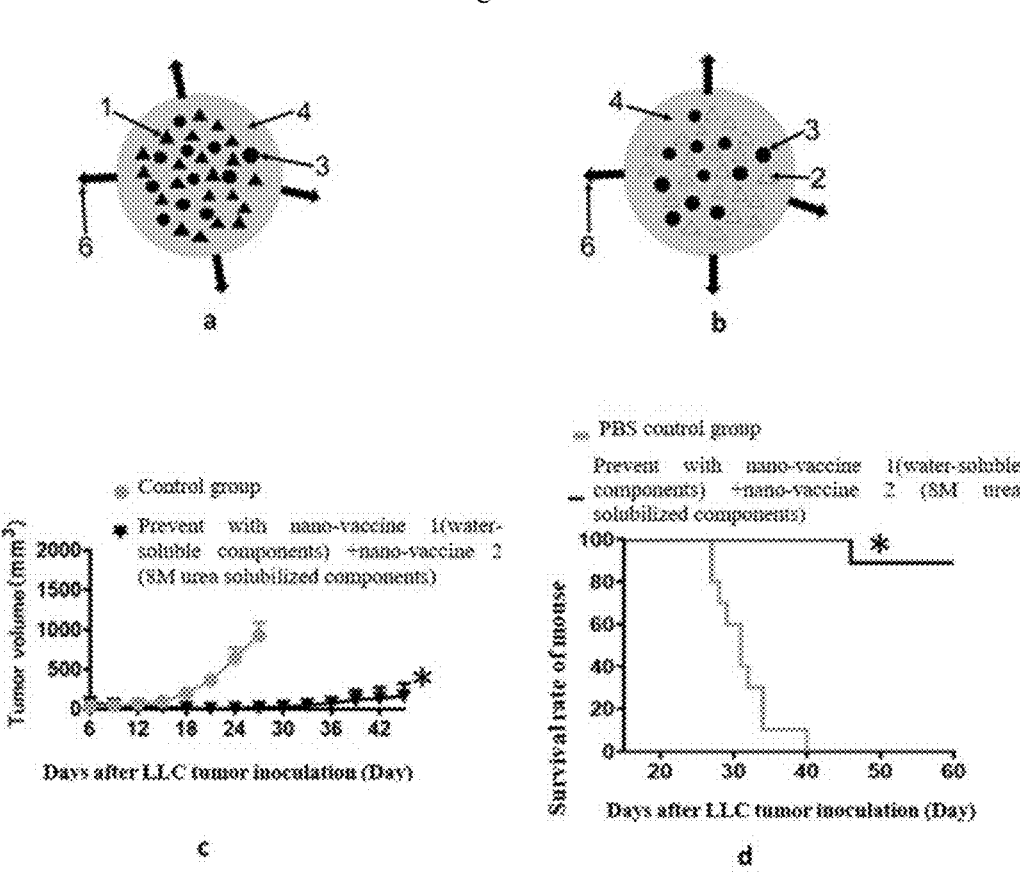

As shown in FIG. 16, compared with the PBS blank control group, the tumor growth rate of the mice in the nano-vaccine group was significantly slower (p<0.05) and the survival time of the mice was significantly prolonged (p<0.05). This shows that the nano-vaccine loaded with water-soluble and water-insoluble components of cancer cells has a prevention effect on lung cancer.

Example 5: Mannose-Modified Nanoparticles Loaded with Whole-Cell Components of Breast Cancer Cells Inside Thereof for Cancer Treatment This example uses treatment of breast cancer in mice to illustrate how to prepare a nano-vaccine loaded with whole-cell components, which was then used to treat breast cancer. In this example, 4T1 mouse triple-negative breast cancer cells were used as cancer cells models. 4T1 cells were first lysed to prepare water-soluble and water-insoluble components of 4T1 cells. Then, a nano-vaccine loaded with water-soluble and water-insoluble components of 4T1 cells was prepared by solvent evaporation method, using PLGA and mannose-modified PLGA (50:50) as nanoparticles backbone materials. BCG (*Bacillus* Calmette-Guerin) adjuvants was used as immune adjuvants, and the nano-vaccine was used to treat tumors in 4T1 breast cancer-bearing mice.

(1) Lysis of Cancer Cells and Collection of Components

A certain amount of 4T1 cells were collected. The cells was frozen at −20° C. to −273° C. after the culture medium was removed. A certain amount of ultrapure water was added, and the sample were repeated freeze-thawing together with sonication at least 3 times to destroy and lyse the cells. After the cells were lysed, the lysate was centrifuged at larger than 100 g for larger than 1 minute and the supernatant is the water-soluble components of 4T1 that is soluble in pure water; addition of 8 M urea aqueous solution to solubilize the precipitation portion can convert the water-insoluble components of 4T1 that are insoluble in pure water to being soluble in 8 M urea aqueous solution. The above obtained water-soluble components and the original water-insoluble components solubilized with 8 M urea, originated from the tumor tissues lysate, were original material sources for preparing the nano-vaccine to treat cancer.

(2) Preparation of Nano-Vaccine

The preparation method and materials used for nano-vaccine in this example are basically the same as those of Example 4, except that the LLC cells were replaced with 4T1 cells and the adjuvants was replaced with BCG adjuvants.

(3) Nano-Vaccine for Cancer Treatment

Female BALB/c mice aged 6-8 weeks were selected as model mice for the preparation of 4T1-bearing mice.

The dosage regimen of nano-vaccine group was as follows: 400,000 4T1 cells were inoculated subcutaneously on the lower right side of the back of each mouse on day 0, and 200 μL of 2 mg PLGA nanoparticles loaded with the water-soluble components of the cancer cells lysate both inside and onto the surface+0.5 mg BCG adjuvants, and 200 μL of 2 mg PLGA nanoparticles loaded with the original water-insoluble components solubilized with 8 M urea both inside and onto the surface+0.5 mg BCG adjuvants were subcutaneously administered on day 4, day 7, day 10, day 15 and day 20, respectively.

The dosage regimen of the PBS blank control group was as follows: 400,000 4T1 cells were inoculated subcutaneously on the lower right side of the back of each mouse on day 0, and 400 μL of PBS was injected subcutaneously on day 4, day 7, day 10, day 15 and day 20, respectively.

Blank nanoparticles+cells lysate control group: 400,000 4T1 cells were inoculated subcutaneously on the lower right side of the back of each mouse on day 0. Water-soluble components of cancer cells lysate, the original water-insoluble components of cancer cells lysate solubilized with 8 M urea and the equal amount of BCG and 4 mg PLGA blank nanoparticles were injected subcutaneously on day 4, day 7, day 10, day 15 and day 20, respectively. It should be noted that the above three injections should be administered separately and injected at different sites to avoid adsorption of the free cell lysate onto the surface of the blank nanoparticles.

In the experiment, the size of the tumor volume of the mice was recorded every three days from day 6 onwards. The tumor volume was calculated using the formula $v=0.52*a*b^2$, wherein v is the tumor volume, a is the tumor length and b is the tumor width. A mouse was considered dead and euthanized when its tumor volume exceeded 2000 $mm^3$ in the survival time experiment.

(4) Experimental Results

Figure 17:
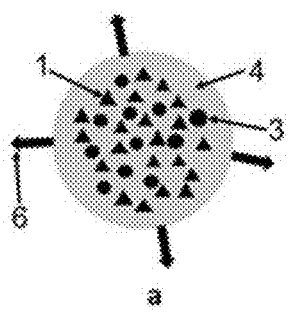
Figure 17:
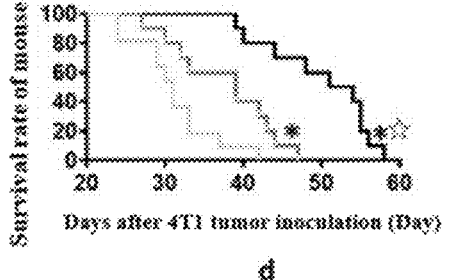
Figure 17:
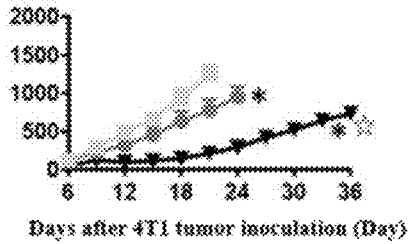
Figure 17:
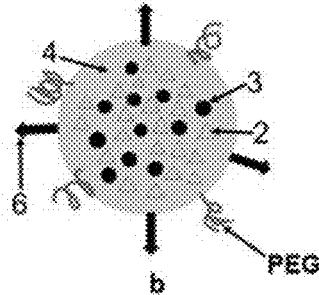

As shown in FIG. 17, compared with the PBS blank control group and the blank nanoparticles+cells lysate control group, the tumor growth rate of the mice in the nano-vaccine group was significantly slower ($p<0.05$) and the survival time of the mice was significantly prolonged ($p<0.05$). This shows that the nano-vaccine loaded with water-soluble and water-insoluble components of cancer cells has a therapeutic effect on breast cancer.

Example 6: Mannose-Modified Nanoparticles Loaded with Whole-Cell Components of Breast Cancer Cells Inside Thereof for Cancer Treatment This example uses treatment of breast cancer in mice to illustrate how to prepare a nano-vaccine loaded with whole-cell components, which was then used to treat breast cancer. In this example, 4T1 mouse triple-negative breast cancer cells were used as cancer cells models. 4T1 cells were first lysed to prepare water-soluble and water-insoluble components of 4T1 cells. Then, a nano-vaccine loaded with water-soluble and water-insoluble components of 4T1 cells was prepared by solvent evaporation method, using PLGA and mannose-modified PLGA (50:50) as nanoparticles backbone materials. BCG adjuvants were used as immune adjuvants, and the nano-vaccine was used to treat tumors in 4T1 breast cancer-bearing mice.

(1) Lysis of Cancer Cells and Collection of Components

The preparation method is the same as that of Example 5.

(2) Preparation of Nano-Vaccine

The preparation method and materials used for nano-vaccine in this example are basically the same as those of Example 5, and whole-cell components were alone loaded inside the nanoparticles. In addition, in the vaccine group containing PEG protective film, during preparation, 3.5% PEG-PLGA was added to the PLGA organic phase (PEG with the molecular weight of 5000, PLGA with the molecular weight of 25000).

(3) Nano-Vaccine for Cancer Treatment

Female BLAB/c mice aged 6-8 weeks were selected as model mice for the preparation of 4T1-bearing mice.

The dosage regimen of nano-vaccine group containing PEG protective film and the nano-vaccine group without PEG protective film was as follows: 400,000 4T1 cells were inoculated subcutaneously on the lower right side of the back of each mouse on day 0, and 200 µL of 2 mg PLGA nanoparticles loaded with the water-soluble components+ 0.5 mg BCG adjuvants, and 200 µL of 2 mg PLGA nanoparticles loaded with water-insoluble components +0.5 mg BCG adjuvants were inoculated subcutaneously on day 4, day 7, day 10, day 15 and day 20, respectively.

The dosage regimen of the PBS blank control group was as follows: 400,000 4T1 cells were inoculated subcutaneously on the lower right side of the back of each mouse on day 0, and 400 µL of PBS was injected subcutaneously on day 4, day 7, day 10, day 15 and day 20, respectively.

In the experiment, the size of the tumor volume of the mice was recorded every three days from day 6 onwards. The tumor volume was calculated using the formula $v=0.52*a*b^2$, wherein v is the tumor volume, a is the tumor length and b is the tumor width.

(4) Experimental Results

Figure 18:
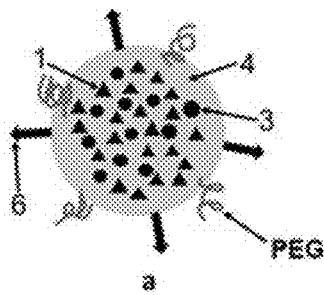
Figure 18:
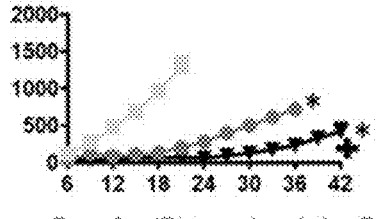
Figure 18:
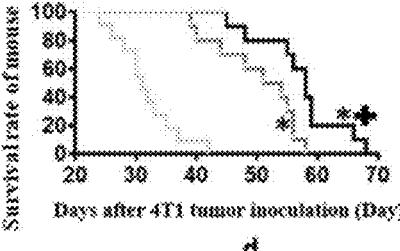

As shown in FIG. 18, compared with the PBS blank control group and the nano-vaccine group without PEG protective film, the tumor growth rate of the mice in the nano-vaccine group containing PEG protective film was significantly slower ($p<0.05$) and the survival time of the mice was significantly prolonged ($p<0.05$). This shows that PEG protective film can protect the nanoparticles from being phagocytosed by cells other than dendritic cells and prolong the circulation time of the nanoparticles in the body, thereby improving the targeting ability and efficacy of the nano-vaccine.

Example 7: Solubilizing Water-Insoluble Components with Different Solubilizers This example uses treatment of breast cancer in mice to illustrate how to prepare a nano-vaccine loaded with whole-cell components, which was then used to treat breast cancer. In this example, 4T1 mouse triple-negative breast cancer cells were used as cancer cells models. 4T1 cells were first lysed to prepare water-soluble and water-insoluble components of 4T1 cells. The water-insoluble components were solubilized with 6 M guanidine hydrochloride and PEG (5000 KD), respectively. Then, a nano-vaccine loaded with water-soluble and water-insoluble components of 4T1 cells was prepared by solvent evaporation method, using PLGA (50:50) and mannose-modified PLGA (50:50) as nanoparticles backbone materials. BCG adjuvants was used as immune adjuvants, and the nano-vaccine was used to treat tumors in 4T1 breast cancer-bearing mice.

(1) Lysis of Cancer Cells and Collection of Components

The preparation method is the same as that of Example 5. The difference is that in this example, 6 M guanidine hydrochloride and PEG (5000 KD) were respectively used to solubilize the water-insoluble components of the lysed cancer cells. The capability of solubilizing water-insoluble components of 6 M guanidine hydrochloride was significantly stronger than PEG (5000 KD): the concentration of the water-insoluble components solubilized with 6 M guanidine hydrochloride came up to 80 mg/mL; the concentration of the water-insoluble components solubilized with PEG (5000 KD) only came up to 1 mg/mL.

(2) Preparation of Nano-Vaccine

The preparation method and materials used for nano-vaccine in this example are basically the same as those of Example 5, and whole-cell components are alone loaded inside the nanoparticles. Moreover, when preparing the nano-vaccine loaded with water-insoluble components, the concentration of the original water-insoluble components solubilized with 6 M guanidine hydrochloride was 60 mg/mL, while the concentration of the original water-insoluble components solubilized with PEG was 1 mg/mL. Therefore, in the prepared nano-vaccines, the nanoparticles loaded with water-insoluble components solubilized with 6 M guanidine hydrochloride had a loading capacity of 70 μg proteins/peptides components, per 1 mg PLGA nanoparticles; the nanoparticles loaded with water-insoluble components solubilized with PEG had a loading capacity of 2 μg proteins/peptides components, per 1 mg PLGA nanoparticles.

(3) Nano-Vaccine for Cancer Prevention

Female BALB/c mice aged 6-8 weeks were selected as model mice for the preparation of 4T1-bearing mice.

The dosage regimen of nano-vaccine group was as follows: 200 μL of 2 mg PLGA nanoparticles (0.5 mg BCG adjuvants), loaded with the water-soluble components of the cancer cells lysate both inside and onto the surface thereof, and 200 μL of 2 mg PLGA nanoparticles (0.5 mg BCG adjuvants), loaded with the original water-insoluble components solubilized with solubilized with 6 M guanidine hydrochloride or PEG, both inside and onto the surface thereof, were subcutaneously administered on day −49, day −42, day −35, day −28 and day −14, before the inoculation of cancer cells, respectively. The PBS control group was injected with 400 μL PBS on the corresponding days. 400,000 4T1 cells were inoculated subcutaneously on the lower right back of each mouse on day 0. In the experiment, the size of the tumor volume of the mice was recorded every three days from day 6 onwards. The calculation of tumor volume is the same as that of Example 1.

(4) Experimental Results

As shown in FIG. 19, compared with the PBS blank control group and the nano-vaccine group containing water-insoluble components solubilized with PEG, the tumor growth rate of the nano-vaccine group containing water-insoluble components solubilized with 6 M guanidine hydrochloride was significantly slower (p<0.05) and the survival time of the mice was significantly prolonged (p<0.05). This shows that solubilizing solutions and solubilizing methods are critical for improving the efficacy of nano-vaccine.

The description above is only for understanding the method of the present invention and core idea thereof. It should be pointed out that for those skilled in the art, the present invention can be improved and modified without departing from the principle of the present invention. Such improvements and modifications also fall within the protection scope of the present invention.

What is claimed is:

1. A targeting delivery system loaded with whole-cell components, wherein it is nano-sized or micron-sized particles with a targeting head on surface thereof, and the particles are loaded with whole-cell components of cancer cells or tumor tissues;

the whole-cell components are water-soluble components and water-insoluble components of whole cells in the cells or tissues; the water-insoluble components are solubilized with a solubilizer or a solubilizing solution containing a solubilizer; the targeting head bonds to molecules on surface of specific cells or tissues to assist the particles to enter cells or tissues.

2. The targeting delivery system of claim 1, wherein the solubilizer can be selected from one or more of urea, guanidine hydrochloride, sodium deoxycholate, SDS, glycerol, alkaline solution with a pH larger than 7, acidic solution with a pH less than 7, albumin, lecithin, Triton, Tween, DMSO, acetonitrile, ethanol, methanol, DMF, propanol, isopropanol, acetic acid, cholesterol, amino acids, glycosides, choline, Brij-35, Octaethylene glycol monododecyl ether, CHAPS, Digitonin, lauryldimethylamine oxide, IGEPAL® CA-630, dichloromethane and ethyl acetate.

3. The targeting delivery system of claim 1, wherein the targeting head is mannose.

4. The targeting delivery system of claim 1, wherein the specific cells or tissues are one or more of dendritic cells, macrophages, B cells, T cells, NK cells, NKT cells, neutrophils, eosinophils granulocytes, basophils, lymph nodes, thymus, spleen and bone marrow.

5. The targeting delivery system of claim 1, wherein the nano-sized particles have a particle size of 1 nm to 1,000 nm; and the micron-sized particles have a particle size of 1 μm to 1,000 μm.

6. The targeting delivery system of claim 1, wherein the nano-sized or micron-sized particles are made of one or more of materials of organic synthetic polymer materials, natural polymer materials, inorganic materials, bacteria or viruses.

7. The targeting delivery system of claim 6, wherein the organic synthetic polymer materials are PLGA, PLA, PGA, Poloxamer, PEG, PCL, PEI, PVA, PVP, PTMC, polyanhydride, PDON, PPDO, PMMA, polyamino acids, synthetic peptides;

the natural polymer materials are phospholipid, cholesterol, starch, carbohydrate, peptides, sodium alginate, albumin, collagen, gelatin, and cell membrane components;

the inorganic materials are ferric oxide, ferroferric oxide, calcium carbonate, and calcium phosphate.

8. The targeting delivery system of claim 1, wherein the targeting delivery system is spherical, ellipsoidal, barrel-shaped, polygonal, rod-shaped, flaky, linear, worm-shaped, square, triangular, butterfly-shaped or dish-shaped.

9. The targeting delivery system of claim 1, which further comprising immune adjuvants.

10. The targeting delivery system of claim 9, wherein the immune adjuvants are one or more of pattern recognition receptor agonist, Bacille Calmette-Guérin (BCG) vaccine, immune adjuvants CpG, immune adjuvants poly(I:C), BCG cell wall skeleton, residues from methanol extraction of BCG, BCG muramyl dipeptide, *Mycobacterium phlei*, polyresistin, mineral oil, virus-like particles, immune enhanced reconstituted influenza virus bodies, cholera enterotoxin, saponin and derivatives thereof, Resiquimod, thymosin, newborn bovine liver active peptides, imiquimod, polysaccharide, curcumin, immune adjuvants poly ICLC, *Corynebacterium parvum* vaccine, *Streptococcus hemolyticus* preparations, coenzyme Q10, levamisole, polyinosinic acid, interleukin, interferon, polyinosinic acid, polyadenosinic acid, alum, aluminium phosphate, lanolin, vegetable oil, endotoxin, liposome adjuvants, GM-CSF, MF59, double-stranded RNA, double strand DNA, aluminium hydroxide, CAF01, active ingredients of *ginseng* and *Astragalus membranaceus*.

11. The targeting delivery system of claim 10, wherein the immune adjuvants are BCG, poly(I:C) and CpG.

12. The targeting delivery system of claim 11, wherein the concentration of BCG, poly(I:C) and CpG is larger than 1 ng/ml.

13. The targeting delivery system of claim 1, wherein a PEG protective film is further added outside the particles.

14. The targeting delivery system of claim 1, wherein the water-soluble components is soluble in pure water or an aqueous solution without a solubilizer, and the water-insoluble components is insoluble in pure water; the portion of the water-insoluble components that is insoluble in pure water or an aqueous solution without a solubilizer can be converted to being soluble in an aqueous solution containing a solubilizer; both water-soluble components and water-insoluble components in the whole-cell components can be solubilized with a solubilizer or a solubilizing aqueous solution containing a solubilizer.

15. The targeting delivery system of claim 1, wherein the targeting delivery system is prepared by following steps:

after lysing cancer cells or tissues, the water-soluble components that are soluble in pure water or an aqueous solution without a solubilizer are first obtained, and then the water-insoluble components are solubilized with solubilizer by using a solubilizing aqueous solution containing a solubilizer, then the whole-cell components are loaded inside or/and onto the surface of nanoparticles or micron-particles to prepare targeting delivery system;

or the whole-cell components can be directly solubilized with a solubilizing aqueous solution containing a solubilizer after lysing cells or tissues without collecting the water-soluble and water-insoluble components separately, and the whole cell components solubilized with the solubilizing aqueous solution are used to prepare the targeting delivery system.

16. A method for preventing or treating cancer, wherein the method comprises administrating the targeting delivery system of claim 1 to a subject in need thereof.

17. The method of claim 16, wherein the cancer is solid tumor or hematological tumor, including but not limited to endocrine system tumor, nervous system tumor, reproductive system tumor, digestive system tumor urinary system tumor, immune system tumor, circulatory system tumor, respiratory system tumor, blood system tumor and skin system tumor.

18. A vaccine comprising the targeting delivery system of claim 1.

19. A method for preventing or treating cancer, wherein the method comprises administrating the vaccine of claim 18 to a subject in need thereof.

* * * * *